(12) United States Patent
Byers et al.

(10) Patent No.: US 9,131,831 B2
(45) Date of Patent: Sep. 15, 2015

(54) INTEGRATED LOCKING DEVICE WITH PASSIVE SEALING

(71) Applicant: Boston Scientific Scimed, Inc., Maple Grove, MN (US)

(72) Inventors: Ransom H. Byers, Oakland, CA (US); Alexander E. Dillon, Louisville, KY (US); Thomas C. Kochem, Watertown, MA (US); Dan W. Rice, Gettysburg, PA (US); Allison L. Schmidt, Dothan, AL (US); Gary A. Jordan, Litchfield, NH (US); Douglas Pleskow, Needham, MA (US); Brian Tinkham, South Boston, MA (US)

(73) Assignee: BOSTON SCIENTIFIC SCIMED, INC., Mape Grove, MN (US)

( * ) Notice: Subject to any disclaimer, the term of this patent is extended or adjusted under 35 U.S.C. 154(b) by 162 days.

(21) Appl. No.: 13/722,039

(22) Filed: Dec. 20, 2012

(65) Prior Publication Data
US 2013/0144117 A1 Jun. 6, 2013

Related U.S. Application Data

(63) Continuation of application No. 12/467,962, filed on May 18, 2009, now Pat. No. 8,343,041.

(60) Provisional application No. 61/054,407, filed on May 19, 2008.

(51) Int. Cl.
*A61B 1/00* (2006.01)
*A61B 1/12* (2006.01)
(Continued)

(52) U.S. Cl.
CPC ......... *A61B 1/00137* (2013.01); *A61B 1/00128* (2013.01); *A61B 1/015* (2013.01);
(Continued)

(58) Field of Classification Search
CPC ........... A61B 1/00137; A61B 1/00131; A61B 1/00142; A61B 17/3462; A61B 17/3421; A61B 17/3498; A61B 17/3423; A61B 2017/3419; A61B 1/018; A61B 2017/347; A61B 17/3415; A61B 2017/3441
USPC ........ 600/154, 159, 121; 604/167.01, 167.06, 604/256
See application file for complete search history.

(56) References Cited

U.S. PATENT DOCUMENTS 561,059 A 5/1896 Mitchell et al.
1,204,053 A 11/1916 Moore
(Continued)

FOREIGN PATENT DOCUMENTS

DE 4115007 A1 11/1992
DE 19911911 A1 9/1999
(Continued)

OTHER PUBLICATIONS

Knecht, Gregory L., M.D. et al., "Double-Channel Fistulotome for Endoscopic Drainage of Pancreatic Pseudocyst," Gastrointestinal Endoscopy, vol. 37, No. 3, May/Jun. 1991, pp. 356-357.
(Continued)

*Primary Examiner* — John P Leubecker
*Assistant Examiner* — Arnaldo Torres Diaz
(74) *Attorney, Agent, or Firm* — Seager, Tufte & Wickhem, LLP

(57) ABSTRACT

Endoscope assemblies, biopsy caps, and methods for making and using the same. An example endoscope assembly may include an endoscope having a channel formed therein and a port that provides access to the channel. A cap may be coupled to the port. The cap may include a base having a securing member for securing the cap to the port, an outer shell, a locking member coupled to the outer shell, an inner seal member, and a central opening that extends to the channel. The inner seal member may include a plurality of flaps.

8 Claims, 27 Drawing Sheets

(51) Int. Cl.
- *A61M 5/178* (2006.01)
- *A61M 5/14* (2006.01)
- *A61B 1/015* (2006.01)
- *A61B 1/018* (2006.01)
- *A61M 39/06* (2006.01)
- *A61M 39/10* (2006.01)
- *A61M 39/20* (2006.01)
- *A61B 1/267* (2006.01)
- *A61B 1/273* (2006.01)
- *A61B 1/31* (2006.01)
- *A61B 10/04* (2006.01)

(52) U.S. Cl.
CPC .............. *A61B 1/018* (2013.01); *A61M 39/06* (2013.01); *A61M 39/0606* (2013.01); *A61M 39/1011* (2013.01); *A61M 39/20* (2013.01); *A61B 1/2676* (2013.01); *A61B 1/2733* (2013.01); *A61B 1/2736* (2013.01); *A61B 1/31* (2013.01); *A61B 10/04* (2013.01); *A61M 2039/0686* (2013.01)

(56) References Cited

U.S. PATENT DOCUMENTS

| | | |
|---|---|---|
| 1,213,001 A | 1/1917 | Philips |
| 1,901,731 A | 3/1933 | Buerger |
| 2,623,520 A | 12/1952 | Bamford, Jr. et al. |
| 3,015,869 A | 1/1962 | Rapata |
| 3,536,281 A | 10/1970 | Attore |
| 3,602,228 A | 8/1971 | Cowley |
| 3,677,243 A | 7/1972 | Nerz |
| 4,178,920 A | 12/1979 | Cawood et al. |
| 4,198,958 A | 4/1980 | Utsugi |
| 4,306,562 A | 12/1981 | Osborne |
| 4,326,516 A | 4/1982 | Schultz et al. |
| 4,345,606 A | 8/1982 | Littleford |
| 4,367,905 A | 1/1983 | Nauta |
| 4,411,654 A | 10/1983 | Boarini et al. |
| 4,412,832 A | 11/1983 | Kling et al. |
| 4,474,174 A | 10/1984 | Petruzzi |
| RE31,855 E | 3/1985 | Osborne |
| 4,509,944 A | 4/1985 | King et al. |
| 4,609,370 A | 9/1986 | Morrison |
| 4,653,477 A | 3/1987 | Akui et al. |
| 4,687,470 A | 8/1987 | Okada |
| 4,696,668 A | 9/1987 | Wilcox et al. |
| 4,700,694 A | 10/1987 | Shishido |
| 4,715,360 A | 12/1987 | Akui et al. |
| 4,723,942 A | 2/1988 | Scott |
| 4,738,666 A | 4/1988 | Fuqua et al. |
| 4,748,982 A | 6/1988 | Horzewski et al. |
| 4,762,129 A | 8/1988 | Bonzel |
| 4,771,777 A | 9/1988 | Horzewski et al. |
| 4,781,677 A | 11/1988 | Wilcox et al. |
| 4,787,884 A | 11/1988 | Goldberg |
| D301,365 S | 5/1989 | Gette |
| 4,835,824 A | 6/1989 | Durham |
| 4,844,092 A | 7/1989 | Rydell et al. |
| 4,858,810 A | 8/1989 | Intlekofer et al. |
| 4,867,605 A | 9/1989 | Myers et al. |
| 4,900,184 A | 2/1990 | Cleveland |
| 4,905,667 A | 3/1990 | Foerster et al. |
| 4,909,798 A | 3/1990 | Fleischhacker et al. |
| 4,917,103 A | 4/1990 | Gambale et al. |
| 4,920,953 A | 5/1990 | McGown |
| 4,927,418 A | 5/1990 | Dake et al. |
| 4,928,669 A | 5/1990 | Sullivan |
| 4,928,693 A | 5/1990 | Goodin et al. |
| 4,932,413 A | 6/1990 | Shockey et al. |
| 4,940,062 A | 7/1990 | Hampton et al. |
| 4,946,443 A | 8/1990 | Hauser et al. |
| 4,973,329 A | 11/1990 | Park et al. |
| 4,983,168 A | 1/1991 | Moorehead |
| 4,988,356 A | 1/1991 | Crittenden et al. |
| 4,995,872 A | 2/1991 | Ferrara |
| 4,997,421 A | 3/1991 | Palsrok et al. |
| 5,026,366 A | 6/1991 | Leckrone et al. |
| 5,034,001 A | 7/1991 | Garrison et al. |
| 5,040,548 A | 8/1991 | Yock et al. |
| 5,061,273 A | 10/1991 | Yock et al. |
| 5,064,414 A | 11/1991 | Revane |
| 5,098,064 A | 3/1992 | Daly et al. |
| 5,106,054 A | 4/1992 | Mollenauer et al. |
| 5,125,915 A | 6/1992 | Berry et al. |
| 5,127,393 A | 7/1992 | McFarlin et al. |
| 5,127,626 A | 7/1992 | Hilal et al. |
| 5,135,535 A | 8/1992 | Kramer et al. |
| 5,137,288 A | 8/1992 | Starkey et al. |
| 5,137,517 A | 8/1992 | Loney et al. |
| 5,139,032 A | 8/1992 | Jahrmarkt et al. |
| 5,147,377 A | 9/1992 | Sahota et al. |
| 5,154,725 A | 10/1992 | Leopold et al. |
| 5,158,545 A | 10/1992 | Trudell et al. |
| 5,160,323 A | 11/1992 | Andrew |
| 5,161,534 A | 11/1992 | Berthiaume |
| 5,163,941 A | 11/1992 | Garth |
| 5,167,634 A | 12/1992 | Corrigan et al. |
| 5,167,636 A | 12/1992 | Clement et al. |
| 5,171,222 A | 12/1992 | Euteneuer et al. |
| 5,180,367 A | 1/1993 | Kontos et al. |
| 5,191,888 A | 3/1993 | Palmer et al. |
| 5,195,978 A | 3/1993 | Schiffer |
| 5,199,948 A | 4/1993 | McPhee |
| 5,205,822 A | 4/1993 | Johnson et al. |
| 5,219,332 A | 6/1993 | Nelson |
| 5,219,335 A | 6/1993 | Willard et al. |
| 5,232,445 A | 8/1993 | Bonzel et al. |
| 5,248,306 A | 9/1993 | Clark et al. |
| 5,250,033 A | 10/1993 | Evans et al. |
| 5,263,932 A | 11/1993 | Jang et al. |
| 5,267,958 A | 12/1993 | Buchbinder et al. |
| 5,279,562 A | 1/1994 | Sirhan et al. |
| 5,281,203 A | 1/1994 | Ressemann et al. |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock et al. |
| 5,304,143 A | 4/1994 | Green et al. |
| 5,306,247 A | 4/1994 | Pfenninger |
| 5,308,318 A | 5/1994 | Plassche |
| 5,314,408 A | 5/1994 | Salmon et al. |
| 5,320,602 A | 6/1994 | Karpiel et al. |
| 5,324,259 A | 6/1994 | Taylor et al. |
| 5,324,269 A | 6/1994 | Miraki et al. |
| 5,328,472 A | 7/1994 | Steinke et al. |
| 5,334,143 A | 8/1994 | Carroll et al. |
| 5,334,147 A | 8/1994 | Johnson et al. |
| 5,334,187 A | 8/1994 | Fischell et al. |
| 5,336,184 A | 8/1994 | Teirstein et al. |
| 5,338,313 A | 8/1994 | Mollenauer et al. |
| 5,342,297 A | 8/1994 | Jang et al. |
| 5,346,498 A | 9/1994 | Greelis et al. |
| 5,350,395 A | 9/1994 | Yock et al. |
| 5,352,215 A | 10/1994 | Thome et al. |
| 5,354,280 A | 10/1994 | Haber et al. |
| 5,357,978 A | 10/1994 | Turk et al. |
| 5,364,355 A | 11/1994 | Alden et al. |
| 5,364,376 A | 11/1994 | Horzewski et al. |
| 5,368,567 A | 11/1994 | Lee et al. |
| 5,370,623 A | 12/1994 | Kreamer |
| 5,380,283 A | 1/1995 | Johnson et al. |
| 5,385,552 A | 1/1995 | Haber et al. |
| 5,387,226 A | 2/1995 | Miraki et al. |
| 5,389,087 A | 2/1995 | Miraki et al. |
| 5,389,100 A | 2/1995 | Bacich et al. |
| 5,391,153 A | 2/1995 | Haber et al. |
| 5,395,335 A | 3/1995 | Jang et al. |
| 5,395,342 A | 3/1995 | Yoon |
| 5,397,302 A | 3/1995 | Weaver et al. |
| 5,397,335 A | 3/1995 | Gresl et al. |
| 5,407,433 A | 4/1995 | Loomas et al. |
| 5,409,459 A | 4/1995 | Gambale et al. |

(56) References Cited

U.S. PATENT DOCUMENTS

| | | | |
|---|---|---|---|
| 5,413,559 A | 5/1995 | Sirhan et al. | |
| 5,415,633 A | 5/1995 | Lazarus et al. | |
| 5,415,639 A | 5/1995 | Vandeneinde et al. | |
| 5,441,486 A | 8/1995 | Yoon et al. | |
| 5,448,993 A | 9/1995 | Lynch et al. | |
| 5,449,363 A | 9/1995 | Brust et al. | |
| 5,451,233 A | 9/1995 | Yock et al. | |
| 5,454,790 A | 10/1995 | Dubrul | |
| 5,456,284 A * | 10/1995 | Ryan et al. | 137/522 |
| 5,458,584 A | 10/1995 | Ginn et al. | |
| 5,458,605 A | 10/1995 | Klemm et al. | |
| 5,460,168 A | 10/1995 | Masubuchi et al. | |
| 5,462,530 A | 10/1995 | Janget et al. | |
| 5,480,389 A | 1/1996 | McWha et al. | |
| 5,489,271 A | 2/1996 | Andersen et al. | |
| 5,490,837 A | 2/1996 | Blaeser et al. | |
| 5,490,859 A | 2/1996 | Mische et al. | |
| 5,496,346 A | 3/1996 | Horzewski et al. | |
| 5,501,227 A | 3/1996 | Yock et al. | |
| 5,531,700 A | 7/1996 | Moore et al. | |
| 5,536,234 A | 7/1996 | Newman et al. | |
| 5,536,248 A | 7/1996 | Weaver et al. | |
| 5,540,236 A | 7/1996 | Ginn | |
| 5,547,469 A | 8/1996 | Rowland et al. | |
| 5,599,299 A | 2/1997 | Weaver et al. | |
| 5,599,300 A | 2/1997 | Weaver et al. | |
| 5,605,162 A | 2/1997 | Mirzaee et al. | |
| 5,613,949 A | 3/1997 | Miraki et al. | |
| 5,626,600 A | 5/1997 | Horzewski et al. | |
| 5,634,475 A | 6/1997 | Wolvek | |
| 5,637,086 A | 6/1997 | Ferguson et al. | |
| 5,645,519 A | 7/1997 | Lee et al. | |
| 5,685,853 A | 11/1997 | Bonnet | |
| 5,693,015 A | 12/1997 | Walker et al. | |
| 5,706,827 A | 1/1998 | Ehr et al. | |
| 5,707,363 A | 1/1998 | Crawford et al. | |
| 5,709,658 A | 1/1998 | Sirhan et al. | |
| 5,718,680 A | 2/1998 | Kraus et al. | |
| 5,725,504 A | 3/1998 | Collins | |
| 5,755,695 A | 5/1998 | Erickson et al. | |
| 5,765,682 A | 6/1998 | Bley et al. | |
| 5,788,681 A | 8/1998 | Weaver et al. | |
| 5,800,414 A | 9/1998 | Cazal et al. | |
| 5,820,600 A | 10/1998 | Carlson et al. | |
| 5,823,995 A | 10/1998 | Fitzmaurice et al. | |
| 5,833,706 A | 11/1998 | St. Germain et al. | |
| 5,836,306 A | 11/1998 | Duane et al. | |
| 5,842,971 A * | 12/1998 | Yoon | 600/101 |
| 5,843,028 A | 12/1998 | Weaver et al. | |
| 5,849,016 A | 12/1998 | Suhr | |
| 5,851,189 A | 12/1998 | Forber | |
| 5,891,056 A | 4/1999 | Ramzipoor | |
| 5,919,004 A | 7/1999 | Christenson | |
| 5,921,971 A | 7/1999 | Agro et al. | |
| 5,931,833 A | 8/1999 | Silverstein et al. | |
| 5,935,114 A | 8/1999 | Jang et al. | |
| 5,978,699 A | 11/1999 | Fehse et al. | |
| 6,007,522 A | 12/1999 | Agro et al. | |
| 6,053,861 A | 4/2000 | Grossi | |
| RE36,702 E | 5/2000 | Green | |
| 6,093,176 A | 7/2000 | Dennis | |
| 6,096,009 A | 8/2000 | Windheuser et al. | |
| 6,106,487 A | 8/2000 | Duane et al. | |
| 6,117,070 A * | 9/2000 | Akiba | 600/154 |
| 6,152,910 A | 11/2000 | Agro et al. | |
| 6,190,333 B1 | 2/2001 | Valencia | |
| 6,190,358 B1 | 2/2001 | Fitzmaurice et al. | |
| 6,200,262 B1 | 3/2001 | Ouchi | |
| 6,245,437 B1 | 6/2001 | Shiiki et al. | |
| 6,254,529 B1 | 7/2001 | Ouchi | |
| 6,277,100 B1 | 8/2001 | Raulerson | |
| 6,312,404 B1 | 11/2001 | Agro et al. | |
| 6,322,577 B1 | 11/2001 | McInnes | |
| 6,346,093 B1 | 2/2002 | Allman et al. | |
| 6,517,518 B2 | 2/2003 | Nash et al. | |
| 6,520,951 B1 | 2/2003 | Carrillo, Jr. et al. | |
| 6,582,401 B1 | 6/2003 | Windheuser et al. | |
| 6,602,240 B2 | 8/2003 | Hermann et al. | |
| 6,606,515 B1 | 8/2003 | Windheuser et al. | |
| 6,607,529 B1 | 8/2003 | Jones et al. | |
| 6,663,597 B1 | 12/2003 | Windheuser et al. | |
| 6,663,598 B1 | 12/2003 | Carrillo, Jr. et al. | |
| 6,679,872 B2 | 1/2004 | Turovskiy et al. | |
| 6,746,442 B2 | 6/2004 | Agro et al. | |
| 6,746,466 B2 | 6/2004 | Eidenschink et al. | |
| 6,764,484 B2 | 7/2004 | Richardson et al. | |
| D498,992 S | 11/2004 | Bloom | |
| 6,827,683 B2 | 12/2004 | Otawara | |
| 6,827,718 B2 | 12/2004 | Hutchins et al. | |
| 6,846,320 B2 | 1/2005 | Ashby et al. | |
| 6,851,424 B2 | 2/2005 | Scopton | |
| 6,863,661 B2 | 3/2005 | Carrillo, Jr. et al. | |
| 6,869,416 B2 | 3/2005 | Windheuser | |
| 6,879,854 B2 | 4/2005 | Windheuser et al. | |
| 6,893,393 B2 | 5/2005 | Carrillo | |
| 6,925,323 B2 | 8/2005 | Snoke | |
| 6,997,908 B2 | 2/2006 | Carrillo, Jr. et al. | |
| 7,009,837 B2 | 3/2006 | Lo | |
| 7,037,293 B2 | 5/2006 | Carrillo et al. | |
| 7,060,052 B2 | 6/2006 | Windheuser et al. | |
| 7,076,285 B2 | 7/2006 | Windheuser et al. | |
| 7,160,283 B2 | 1/2007 | Richardson et al. | |
| 7,172,577 B2 | 2/2007 | Mangano et al. | |
| 7,178,520 B2 | 2/2007 | Scopton | |
| 7,179,252 B2 | 2/2007 | Agro et al. | |
| 7,537,583 B2 | 5/2009 | Carrillo, Jr. et al. | |
| 7,637,863 B2 | 12/2009 | Deal et al. | |
| 7,645,266 B2 | 1/2010 | Carrillo, Jr. et al. | |
| 7,670,316 B2 | 3/2010 | Windheuser et al. | |
| 7,803,107 B2 | 9/2010 | Carrillo | |
| 8,206,320 B2 | 6/2012 | Deal et al. | |
| 8,636,686 B2 * | 1/2014 | Minnelli et al. | 604/26 |
| 2001/0029362 A1 | 10/2001 | Sirhan et al. | |
| 2002/0007152 A1 | 1/2002 | Hermann et al. | |
| 2002/0016612 A1 | 2/2002 | Ashby et al. | |
| 2003/0088153 A1 | 5/2003 | Carrillo, Jr. et al. | |
| 2003/0208104 A1 | 11/2003 | Carrillo, Jr. et al. | |
| 2003/0233043 A1 | 12/2003 | Windheuser et al. | |
| 2004/0106852 A1 | 6/2004 | Windheuser et al. | |
| 2004/0111060 A1 * | 6/2004 | Racenet et al. | 604/167.01 |
| 2004/0162465 A1 | 8/2004 | Carrillo | |
| 2004/0193142 A1 | 9/2004 | Agro et al. | |
| 2005/0059890 A1 | 3/2005 | Deal et al. | |
| 2005/0090835 A1 | 4/2005 | Deal et al. | |
| 2005/0148820 A1 | 7/2005 | Carrillo | |
| 2005/0165277 A1 | 7/2005 | Carrillo et al. | |
| 2005/0203543 A1 | 9/2005 | Hilal | |
| 2006/0041189 A1 * | 2/2006 | Vancaillie | 600/154 |
| 2006/0135978 A1 | 6/2006 | Franer | |
| 2006/0142734 A1 | 6/2006 | Carrillo et al. | |
| 2006/0149128 A1 * | 7/2006 | Baror | 600/104 |
| 2006/0195117 A1 | 8/2006 | Rucker et al. | |
| 2006/0217665 A1 * | 9/2006 | Prosek | 604/167.02 |
| 2006/0229496 A1 | 10/2006 | Windheuser et al. | |
| 2007/0238928 A1 | 10/2007 | Maseda et al. | |
| 2007/0244356 A1 | 10/2007 | Carrillo et al. | |
| 2007/0293719 A1 | 12/2007 | Scopton et al. | |
| 2008/0194913 A1 | 8/2008 | Tinkham et al. | |
| 2008/0290605 A1 * | 11/2008 | Brockmeier et al. | 277/355 |
| 2009/0076464 A1 * | 3/2009 | Gresham | 604/264 |
| 2009/0203960 A1 | 8/2009 | Carrillo et al. | 600/104 |
| 2009/0275880 A1 * | 11/2009 | Pasqualucci | 604/26 |
| 2011/0021977 A1 | 1/2011 | Pasqualucci | 604/26 |
| 2012/0004507 A1 * | 1/2012 | Kaye | 600/154 |

FOREIGN PATENT DOCUMENTS

| | | |
|---|---|---|
| DE | 19916866 A1 | 10/1999 |
| EP | 0328760 A2 | 8/1989 |
| EP | 0388112 A2 | 9/1990 |
| EP | 0792657 A2 | 9/1997 |
| EP | 0801955 B1 | 10/1997 |
| EP | 1779764 A1 | 5/2007 |
| JP | 50108287 U | 9/1975 |

(56) References Cited

FOREIGN PATENT DOCUMENTS

| JP | 3126428 | A | 5/1991 |
|---|---|---|---|
| JP | 623055 | A | 2/1994 |
| JP | 7155382 | A | 6/1995 |
| JP | 994253 | A | 4/1997 |
| WO | 9203963 | A1 | 3/1992 |
| WO | 9613296 | A1 | 5/1996 |
| WO | 9633764 | A1 | 10/1996 |
| WO | 9810820 | A1 | 3/1998 |
| WO | 9810821 | A1 | 3/1998 |
| WO | 9938557 | A1 | 8/1999 |
| WO | 9959664 | A1 | 11/1999 |
| WO | 0069499 | A1 | 11/2000 |
| WO | 0069500 | A1 | 11/2000 |

OTHER PUBLICATIONS

Siegel, Jerome H., M.D. et al., "Two New Methods for Selective Bile Duct Cannulation and Sphincterotomy," Gastrointestinal Endoscopy, vol. 33, No. 6, Dec. 1987, pp. 438-440.

* cited by examiner

INTEGRATED LOCKING DEVICE WITH PASSIVE SEALING

CROSS-REFERENCE TO RELATED APPLICATIONS

This application is a continuation of U.S. patent application Ser. No. 12/467,962, filed May 18, 2009, now U.S. Pat. No. 8,343,041, which claims the benefit of U.S. Provisional Application No. 61/054,407, filed May 19, 2008, the entire disclosures of which are incorporated herein by reference in their entireties.

This application is related to U.S. patent application Ser. No. 12/467,971, filed May 18, 2009, which claims the benefit of U.S. Provisional Application Ser. No. 61/054,393, filed May 19, 2008; U.S. patent application Ser. No. 12/467,968, filed May 18, 2009, which claims the benefit of U.S. Provisional Application No. 61/054,413, filed May 19, 2008; and U.S. patent application Ser. No. 12/467,947, filed May 18, 2009, which claims the benefit of U.S. Provisional Application Ser. No. 61/054,294, filed May 19, 2008, which disclosures are all hereby incorporated herein by reference in their entireties. This application is also related to U.S. patent application Ser. No. 12/029,148, filed Feb. 11, 2008, the disclosure of which is hereby incorporated herein by reference.

FIELD OF THE INVENTION

The present invention pertains to endoscopes, endoscope assemblies, guidetubes, introducers, and instrument caps for endoscopes, guidetubes, and introducers. More particularly, the present invention pertains to biopsy caps for an access port of an endoscope.

BACKGROUND

A wide variety of endoscope assemblies and biopsy caps have been developed. Of the known endoscope assemblies and biopsy caps, each has certain advantages and disadvantages. There is an ongoing need to provide alternative endoscope assemblies and biopsy caps as well as methods for making and using the same.

BRIEF SUMMARY

The invention provides design, material, and manufacturing method alternatives for endoscope assemblies and biopsy caps as well as provides methods for making and using endoscope assemblies and biopsy caps.

An example endoscope assembly may include an endoscope having a channel formed therein and a port that provides access to the channel. A cap may be coupled to the port. The cap may include a base having a securing member for securing the cap to the port, an outer shell, a locking member coupled to the shell, an inner seal member disposed within the shell, and one or more openings extending through the cap and into the channel. The inner seal member may include a plurality of flaps.

An example endoscope biopsy cap may include an outer shell having an opening formed therein and a base. A securing member may be disposed on the base for securing the base to a port on an endoscope. A locking member may be coupled to the shell for securing the position of a medical device disposed in the opening. A multi-layer inner seal member may be disposed within the shell.

Another example endoscope biopsy cap may include an outer shell having an opening formed therein and a base. A securing member may be disposed on the base for securing the base to a port on an endoscope. A locking member may be coupled to the shell for securing the position of a medical device disposed in the opening. A plurality of sealing members may be disposed within the shell.

Another example endoscope biopsy cap may include an outer shell having an opening formed therein and a base. A securing member may be disposed on the base for securing the base to a port on an endoscope. A locking member may be coupled to the shell for securing the position of a medical device disposed in the opening. A sealing member may be disposed within the shell. The sealing member may include a pair of openings extending therethrough.

An example method for using an endoscope may include providing an endoscope having a channel formed therein and a port that provides access to the channel, disposing the endoscope within a body lumen of a patient, and disposing a cap on the port. The cap may include an outer shell having an opening formed therein and a base. A securing member may be disposed on the base for securing the base to the port. A locking member may be coupled to the shell for securing the position of a medical device disposed in the opening. An inner seal member may be disposed within the shell. The inner seal member may include a plurality of flaps.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
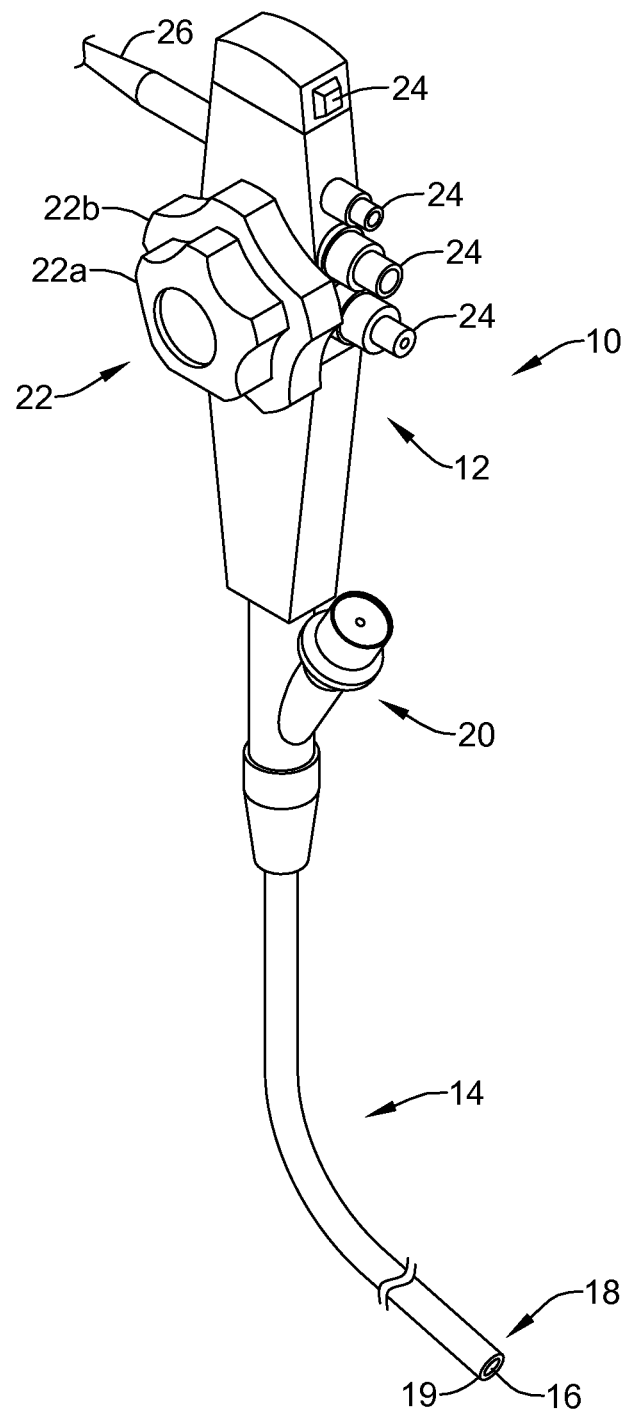
FIG. 1 is a perspective view of an example endoscope assembly.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

An example endoscope and/or endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guidetubes, introducers (without or without vision or visualization capabilities), or any other type of endoscope or related medical device. Endoscope 10 may include a handpiece 12 and an elongate shaft 14 extending distally from handpiece 12 to a distal tip 18. Shaft 14 may include a lumen defining a working channel 16 extending through shaft 14 from a distal end 19 near distal tip 18 of shaft 14 to an access port 20 that may be positioned in handpiece 12 or another portion of endoscope 10. Although endoscope 10 is depicted with a single working channel in FIG. 1, it can be appreciated that in other embodiments, endoscope 10 may include multiple working channels, as desired.

Handpiece 12 may include one or a plurality of controls 22, such as rotating knobs, which may be used to control movement of distal tip 18 of shaft 14 during operation. For example, a first rotating knob 22a may control up and down movement or deflection of distal tip 18 of shaft 14, while a second rotating knob 22b may control side-to-side movement or deflection of distal tip 18 of shaft 14. Handpiece 12 may also include one or a plurality of buttons 24, which may be used to activate suction or deliver fluid such as air, saline and/or water, etc. through a lumen of the endoscope 10 or perform other functions as desired. Additionally, handpiece 12 may include an optical cable 26 connected to an external light source (not shown).

Figure 2:
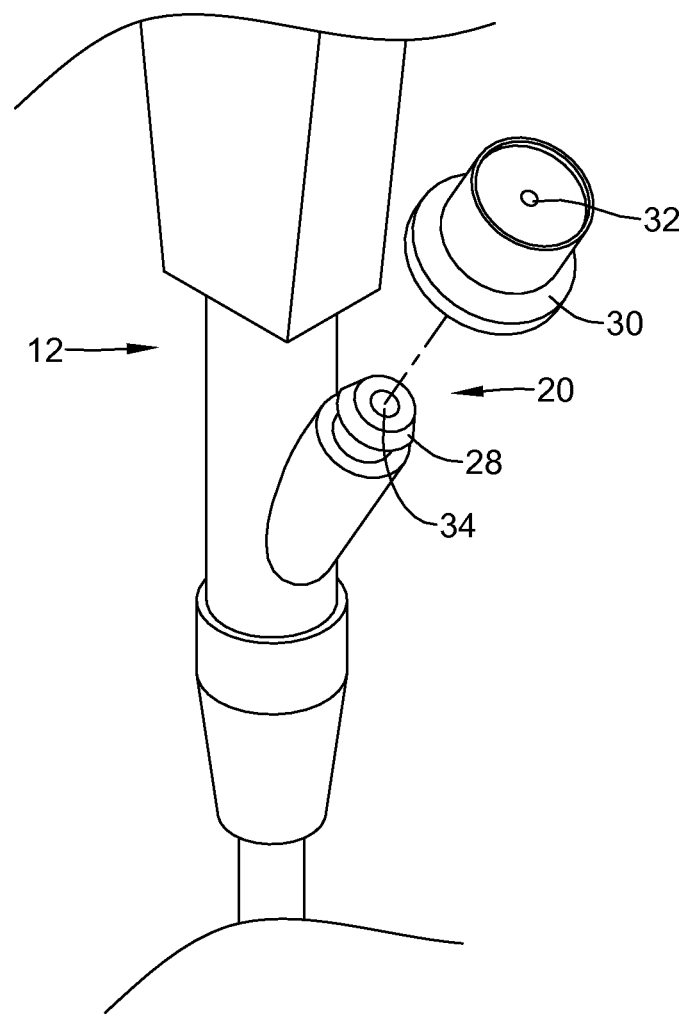
FIG. 2 is an exploded view of a portion of the example endoscope assembly shown in FIG. 1 illustrating a biopsy cap.

Turning now to FIG. 2, here access port 20 of handpiece 12, which provides access to working channel 16 of endoscope 10, is illustrated. Access port 20, which may extend from the side of endoscope 10 or at another location, may include a coupling portion 28 for coupling a cap 30 to access port 20. Cap 30, which may be removably attached or permanently attached to access port 20, may provide access for inserting and/or advancing an endoscopic device through working channel 16 of endoscope 10.

Caps like cap 30, which may be termed "biopsy caps", are often designed with several functions in mind. For example, cap 30 may form a fluid/air barrier to working channel 16 that may help control insufflation and bile fluid egress therefrom that later have the potential to spill onto the clinician's hands and/or the floor thereby interfering with the intervention and/or become a biohazard. In addition, cap 30 may have an opening 32 extending therethrough. Opening 32 may be in fluid communication with working channel 16 and it may reduce the size of the opening 34 of working channel 16, for example, to accommodate an endoscopic device or instrument. Thus, caps like cap 30 may be much like an adapter in that it forms a physical transition at opening 34 of working channel 16 (or other instrument channels or access points) so that it transitions to a size more closely to that of the device to be inserted into working channel 16. Some additional discussion regarding biopsy caps can be found in U.S. Patent Application Pub. Nos. US20070293719A1, US20070244356A1, and US20070238928A1, the entire disclosures of which are herein incorporated by reference.

A number of additional biopsy caps are contemplated that incorporate at least some of the desirable features of biopsy caps as well as have other desirable characteristics. The forgoing discussion discloses some of the embodiments of caps that are contemplated. These caps may include a passive seal.

For the purposes of this disclosure, a passive seal is a seal that seals endoscope 10 at port 20 so as to prevent the leakage of bodily fluids and/or air. In addition, by virtue of being "passive", the caps disclosed herein are configured to seal off endoscope 10 at port 20 without the need of any so-called "active" processes or steps by the clinician.

Figure 3:
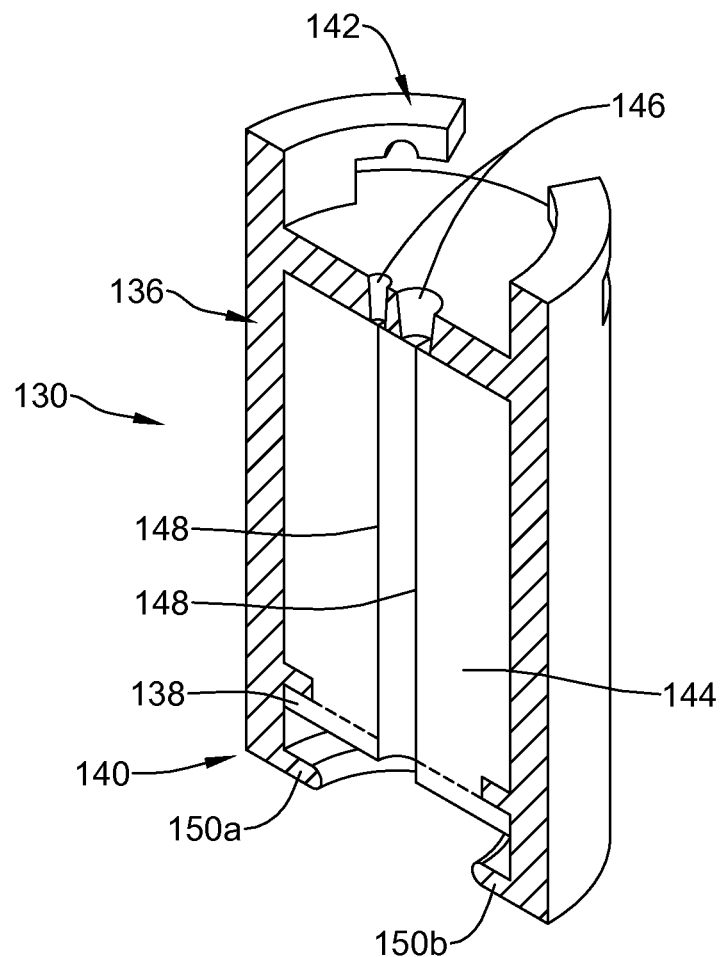
FIG. 3 is a cross-sectional view of another example biopsy cap.

Turning now to the remaining figures, FIG. 3 is a partial cross-sectional side view of biopsy cap 130, which may be similar in form and function to other caps disclosed herein. Here it can be seen that cap 130 may include an outer shell 136, a securing member 140 that may help to secure cap 130 to port 20, one or more locking members 142 coupled to shell 136, and an inner seal member 144 disposed within outer shell 136. Outer shell 136 may take a number of different shapes and forms. In general, however, outer shell 136 may be made from a relatively rigid or hard polymer/plastic, a metal or metal alloy, a ceramic, and the like, or combinations thereof and may take a form resembling an exoskeleton or protective covering over the more delicate interior (e.g., seal member 144). In addition, by virtue of forming outer shell 136 from a relatively rigid material, a number of accessories to and/or structural components of cap 130 may be secured to or integrally formed with shell 136. For example, securing member 140 and/or locking members 142 may be secured to or integrally formed with outer shell 136.

Outer shell 136 may have one or more apertures 146 formed therein. Apertures 146, for example, may be disposed on a top surface or surface that is opposite securing member 140, although any other suitable portion of outer shell 136 may include apertures 146 including the sides or side surfaces. Apertures 146 may be the entrance point or otherwise define one or more openings that extend through cap 130 into channel 16 when cap 130 is seated on port 20. For example, apertures 146 may extend through outer shell 136 and provide access to slits 148, which may be formed in seal member 144. Thus, apertures 146 may form the exterior opening in cap 130 where other medical devices (e.g., guidewires, catheters, etc.) can be passed through so as to gain access to working channel 16 via slits 148.

To ease the ability of a user to pass a medical device through apertures 146, apertures 146 may have a chamfered or beveled edge, which may function like a funnel to guide the medical device into aperture. In addition to the funneling function that may be realized by the inclusion of beveled apertures 146, apertures 146 may also provide cap 130 with a number of additional desired characteristics. For example, because apertures 146 are formed in the relatively rigid outer shell 136 and because they are generally positioned a distance away from port 20, apertures 146 and/or outer shell 136 may also function as a strain relief that may relieve strain that might otherwise be applied to endoscope 10 (e.g., at port 20), for example, during device exchanges or transfers. Thus, the shear stress that may be generated during device exchanges can be shifted away from endoscope 10, which may improve the ability of cap 130 to maintain a good seal at port 20.

Securing member 140 may be disposed on a bottom surface of cap 130. In some embodiments, a sealing disk or sleeve 138 may be disposed adjacent securing member 140. Disk 138 may desirably impact the seal formed between cap 130 and port 20. Securing member 140 may take any number of a wide array of forms including those disclosed herein. For example, securing member 140 may include a pair of tabs 150a/150b, which may snap onto or otherwise secure to port 20. Securing tabs 150a/150b onto port 20 may include, for example, snapping tabs 150a/150b onto a narrowed ring or portion of port 20. This may include snapping tabs 150a/150b onto port from a peripheral or side region of port 20. In addition, a portion of shell 136 may include a cutout or notch (not shown) that may provide some structural relief for securing member 140 and that may allow tabs 150a/150b to have greater flexibility when securing cap 130 to port 20. The precise form of securing member 140 and/or tabs 150a/150b may vary. For example, a different number of tabs may be utilized, differently shaped tabs may be utilized or a different securing system altogether may be utilized for securing cap 130 to port 20. Furthermore, various adaptors may be provided to create a suitable connection between cap 130 and port 20 if such a connection cannot be easily made with tabs 150a/150b or another suitable securing member 140. Examples of some of the various alternative securing members 140 contemplated can be found below.

Locking members 142 may be generally disposed adjacent the top surface of cap 130 and they may be used to secure and/or hold the position of a device (e.g., a guidewire, catheter, etc.) extending through cap 130 into channel 16. However, locking members 142 may be disposed on any suitable surface of cap 130 and/or shell 136. Locking members 142 may also be integrally formed with shell 136. In addition to holding the position of a device, locking members 142 may also tend to guide these devices away from the center of cap 130 so that other device may gain access to channel 16 via cap 130. In at least some embodiments, locking members 142 may include one or more bends or "hooks" formed therein that a medical device may be wrapped around or pressed against to hold its position. The number of locking members 142 may vary. In some embodiments, one locking member 142 is utilized. In other embodiments, two, three, four, five, six, or more locking members 142 are utilized. In addition, the precise form of locking members 142 may also vary. For example, locking member 142 may or may not include a wing or flap that may tend to direct a device toward locking member 142. Examples of some of the various alternative locking members 142 contemplated can be found below.

Seal member 144 may comprise a soft material such as a plastic or foam that may be suitable for sealing about a medical device extending therethrough. The precise form and materials for seal member 144 may vary. For example, seal member 144 may include a pliable or formable material that may or may not be absorbent. In some embodiments, seal member 144 may include those materials used for similar structures disclosed in U.S. Pat. No. 6,663,598, the entire disclosure of which is herein incorporated by reference. In at least some embodiments, seal member 144 may substantially fill the interior of shell 136. Alternatively, a portion of the interior of shell 136 may lack seal member 144 and may be used, for example, to hold bodily fluids that may escape from port 20. In still further embodiments, a portion of seal member 144 may extend out from shell 136 and it may define or otherwise function as a strain relief As indicated above, seal member 144 may have one or more slits 148 extending therethrough. Accordingly, medical device(s) may be advanced through apertures 146, through slits 148, and into working channel 16 for use as part of a medical intervention. The precise number of slits 148 may vary. For example, seal member 144 may include one, two, three, four, five, six, or more slits 148. In embodiments where multiple slits 148 are utilized, seal member 144 may be configured so that each medical device (which may generally have a round cross-sectional shape) can be disposed in its own slit 148. This arrangement may be desirable because it may allow seal member 144 to seal more effectively around each medical device as opposed to the sealing of multiple medical devices through a single slit, which may create gaps adjacent the edges of the devices where bodily fluids may have a chance to escape or otherwise leak from the biopsy cap.

In some embodiments, a portion of seal member 144 (e.g., a portion adjacent apertures 146) may be chamfered so that it may help guide or funnel devices through slits 148. Seal member 144 may extend laterally to the edges (and/or the top) of shell 136. This may help to prevent or reduce the amount of fluids that may migrate into and out from cap 130. Alternatively, a gap may be formed between the top of seal member 144 and the top of the interior of shell 136. The gap may provide an area for fluids to collect that may escape seal member 144 and that may otherwise "splash" during, for example, device removal or exchange.

Figure 4:
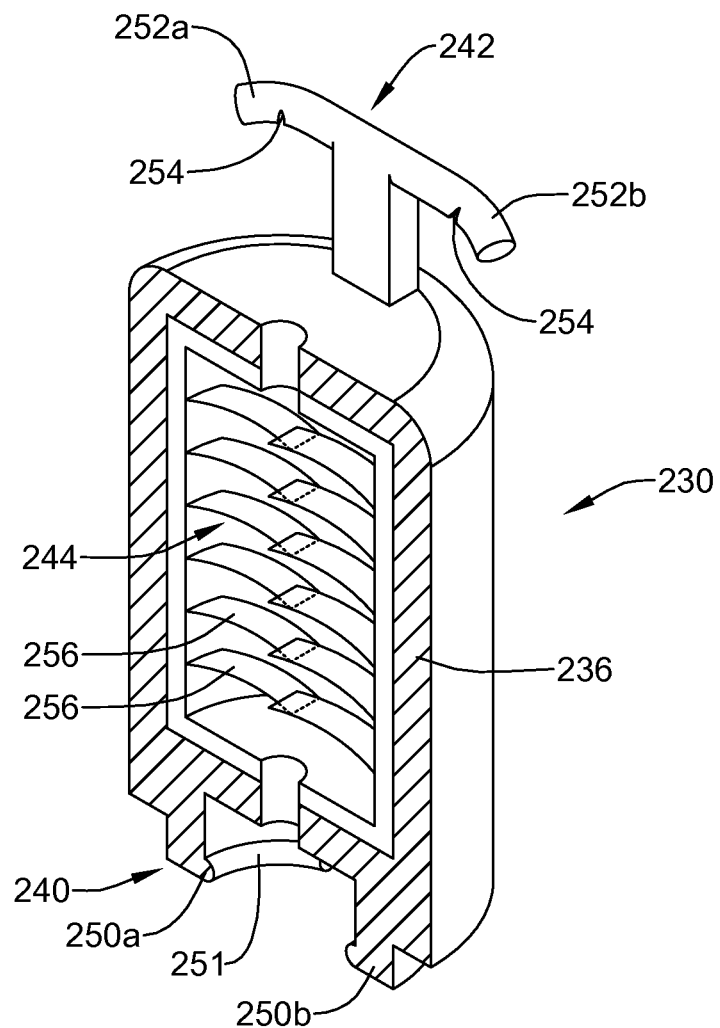
FIG. 4 is a cross-sectional view of another example biopsy cap.

Another example cap 230 is illustrated in FIG. 4. Cap 230 may include shell 236, securing member 240, locking member 242, and seal member 244. Cap 230 may be similar in form and function to other caps disclosed herein. For example, shell 236 may be similar to shell 136. Securing member 240 may be similar to securing member 140 and it may include a pair of locking tabs 250a/250b that each have a lip or ridge 251 that may improve the ability of securing member 240 to attach to port 20. Locking member 242 may include a body that splits into two arms 252a/252b. Each arm 252a/252b may include a wire lock 254, which may take the form of a notch that a medical device (e.g., a guidewire, catheter, etc.) may be wedged into so that its position relative to the cap can be secured. In at least some embodiments, locks 254 may be positioned adjacent a bend or curve defined in arms 252a/252b so that the shape and/or configuration of arms 252a/252b may funnel or direct the medical device toward locks 254. This may simplify the process of disposing the medical device within locks 254.

Seal member 244 may include a plurality of flaps or membranes 256. Flaps 256 may take the form of flexible membranes of material that may press and seal against a device extending therethrough. Flaps 256 may be arranged, for example, in a series of horizontal layers that are stacked vertically. Each layer may include one or more flaps 256 that may or may not overlap with one another. Numerous other arrangements are also contemplated. By arranging flaps 256 in the manner illustrated in FIG. 4, each layer or set of flaps 256 may form a "seal" such that flaps 256 may define a plurality of seals. If one of these seals (e.g., the layer of flaps 256 closest to securing member 240) should be compromised, an adjacent seal would maintain the integrity of seal member 244, and so on. Thus, the multi-layer design of seal member 244 may enhance the ability of cap 230 to prevent the leakage of bodily fluids during a medical intervention.

The number of flaps 256 utilized in seal member 244 as well as the number of layers may vary. For example, each layer may include one, two, three, four, five, six, seven, eight, or more flaps 256. Likewise, seal member 244 may include one, two, three, four, five, six, seven, eight, or more layers of flaps 256. In some embodiments, each layer may include the same number of flaps 256. In other embodiments, differing numbers of flaps 256 may be used in different layers.

FIGS. 5-8 illustrate other example caps, which may be similar in form and function to other caps disclosed herein that utilize different seal members. Some of the example securing members and locking members that may be utilized for these caps are omitted from the drawings for simplicity purposes. It can be appreciated that these caps may utilize any suitable securing member, locking member, or other structure(s), as appropriate, without departing from the spirit of the invention.

Figure 5:
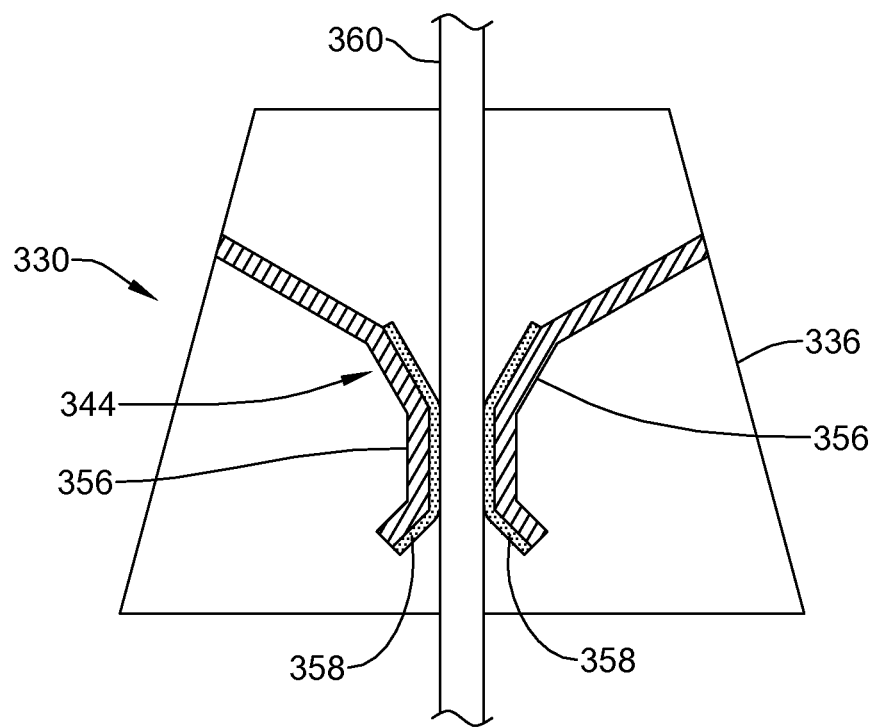
FIG. 5 is a partial cross-sectional side view of another example biopsy cap.

Turning now to FIG. 5, here cap 330 can be seen. Cap 330 may include seal member 344, which may include a plurality of fingers 356 that each may have a pad 358 attached thereto. Pads 358 may include any suitable material including a sealing foam, a sealing polymer/plastic, any other suitable material for sealing, and the like. In some embodiments, pads 358 may structurally extend into two planes so that they have a shape that helps to "funnel" or guide a device through fingers 356. Fingers 356 may extend radially inward from shell 336. In at least some embodiments, fingers 356 may be made from a relatively elastic or resilient material that may be biased to extend inward from shell 336. Alternatively, a spring or other biasing structure (including, for example, a living spring or hinge, a spring with a varying pitch, a balloon or inflatable member, and the like) may be used to hold fingers 356 in the desired position. The spring may be designed to hold a relatively constant amount of pressure on fingers 356 so that substantially constant sealing pressure can be transferred onto a device extending therethrough.

When a device 360 (e.g., a guidewire, catheter, etc.) is advanced through cap 330, fingers 356 may seat against and seal around device 360. Because of the configuration of fingers 356, fingers 356 can shift slightly in position to accommodate device 360 (i.e., thereby overcoming a portion of the bias) and then return to their original position. Accordingly, when device 360 is removed, fingers 356 may return to a more radially inward position so as to close off and seal the opening(s) extending through cap 330.

The configuration and arrangement of seal member 344 may vary. For example, in some embodiments, two fingers 356 may be utilized. Alternatively, three, four, five, six, or more fingers 356 may be included. In addition, multiple pads 358 may be included on one or more of fingers 356. In these and other embodiments, fingers 356 may be arranged in essentially any suitable pattern within cap 330 including, for example, a generally circular pattern that forms a point for device 360 to pass through cap 330 and into channel 16. Other arrangements are contemplated including non-circular patterns, patterns with multiple points for device 360 to pass through, etc.

Figure 6:
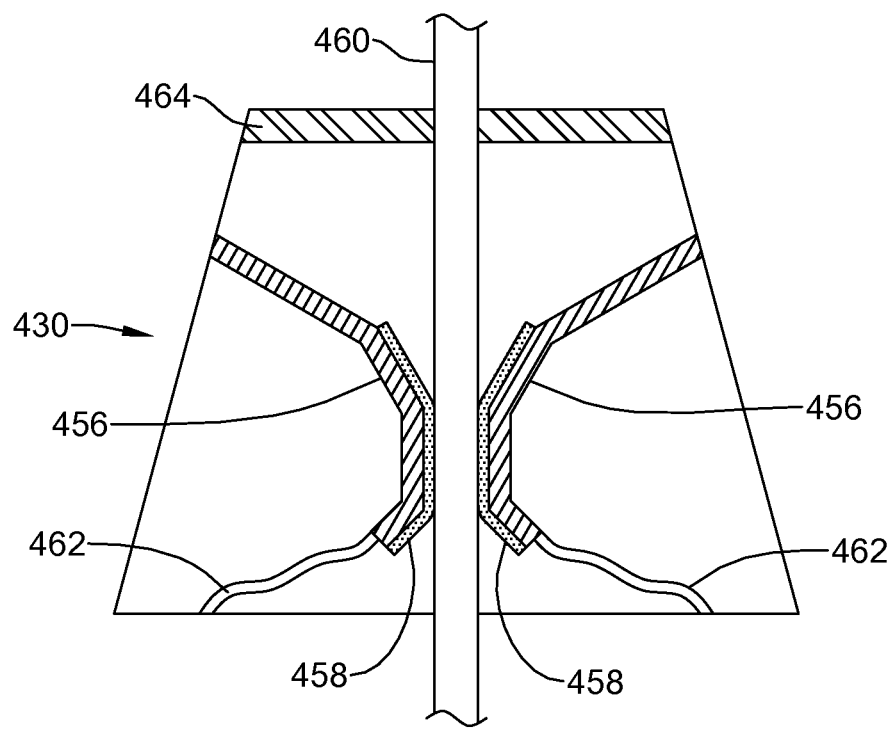
FIG. 6 is a partial cross-sectional side view of another example biopsy cap.

FIG. 6 illustrates another cap 430 that may be similar to cap 330 (and other caps disclosed herein). Cap 430 may include fingers 456 having a sealing material or pads 458 attached thereto. Just like fingers 356, fingers 456 may be biased to extend radially inward to seat against device 460. However, fingers 456 may each include a tether 462 that may, for example, relieve some of the bias and make it easier for device 460 to extend therethrough. In addition, cap 430 may include a top seal 464. Top seal 464 may include any suitable sealing material and may have one or more openings formed therein for device 460 to extend therethrough.

Figure 7:
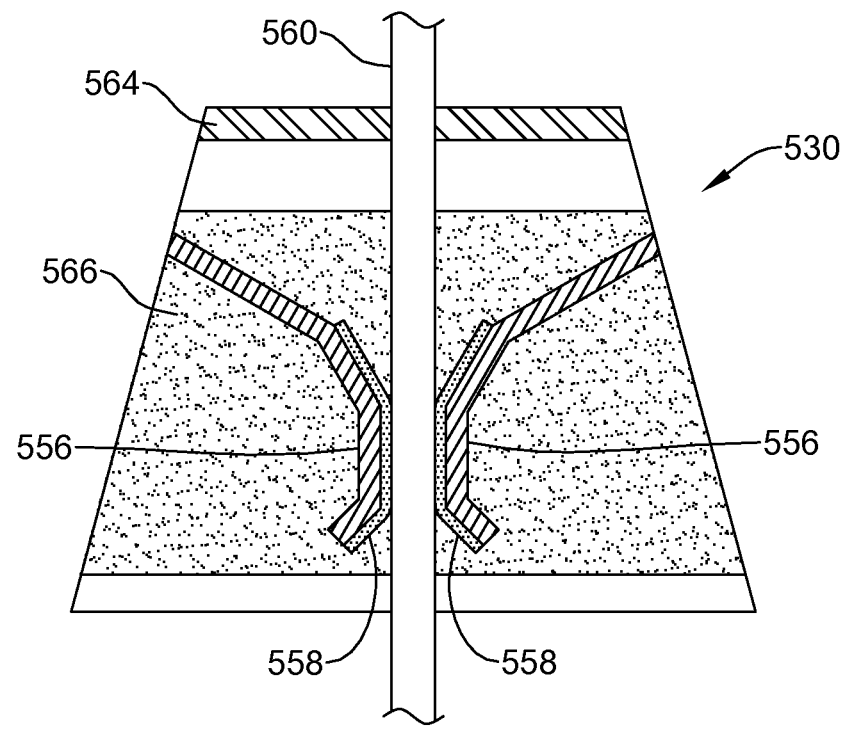
FIG. 7 is a partial cross-sectional side view of another example biopsy cap.

FIG. 7 illustrates another cap 530 that may be similar to other caps disclosed herein. Cap 530 may include fingers 556 having pads 558 attached thereto. Just like fingers 356/456, fingers 556 may be biased to extend radially inward to seat against device 560. Cap 530 may also include a sealing substance, fluid, and/or gel 566 disposed adjacent fingers 556. Gel 556 may help to further prevent unwanted fluid and/or air leakage from cap 530. In some embodiments, gel 566 may include a petroleum jelly or similar substance such as VASELINE® petroleum jelly and/or KY® jelly. Alternatively, gel 566 may include a hygroscopic material that may expand upon absorption of fluids and may place additional sealing force on device 560. In addition, cap 530 may include a top seal 564, which may be similar to seal 464. Furthermore, caps like cap 530 or any other cap disclosed herein may include another sealing feature such as an inflated structure (e.g., an inflatable member or balloon including a hollow cylinder balloon, etc.), a filled structure (e.g., a sealing foam, a sealing coating, etc.), and the like, combinations thereof, or any other suitable feature.

Figure 8:
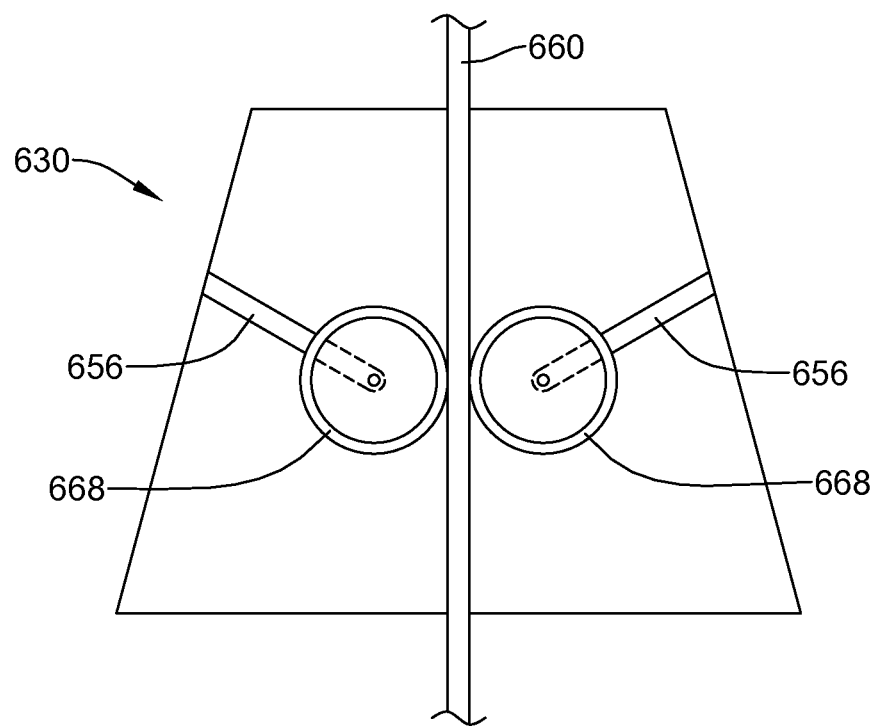
FIG. 8 is a partial cross-sectional side view of another example biopsy cap.

FIG. 8 illustrates another cap 630 that may be similar to other caps disclosed herein. Cap 630 may include fingers 656 having wheels or rollers 668 attached thereto. Besides having wheels 668 attached thereto, fingers 656 may be otherwise similar to fingers 356/456/556. For example, fingers 656 may be biased to extend radially inward and seat against device 660. Wheels 668 may configured to seat against and seal device 660. Because wheels 668 may be able to rotate within cap 630, wheels 668 may improve the ability of device 660 to pass through cap 630 during an intervention and may reduce the friction between wheels 668 and device 660.

Figure 9:
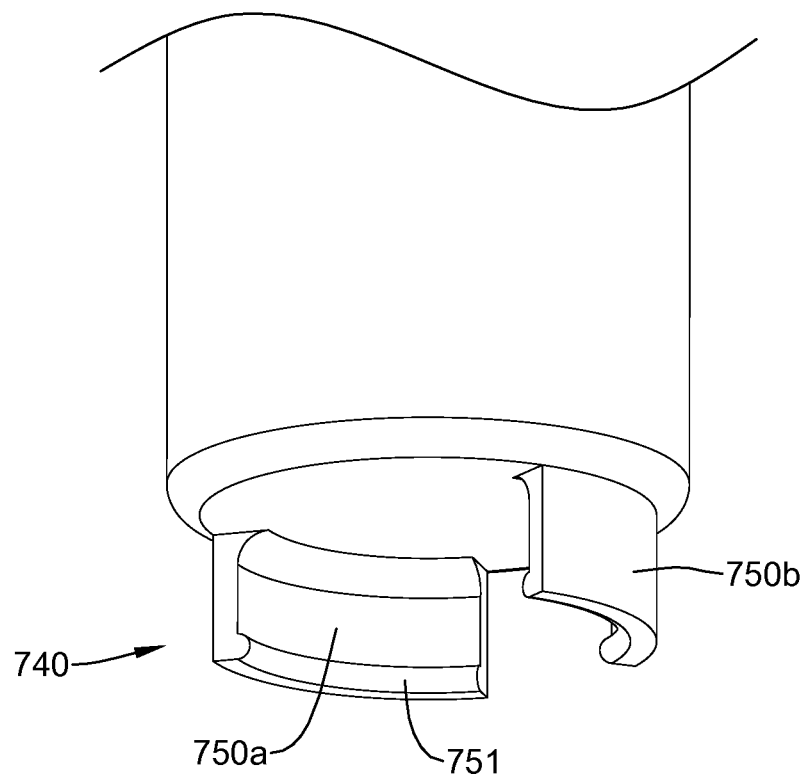
FIG. 9 is a perspective view of an example securing member.

FIGS. 9-15 illustrate some examples of securing members that may be utilized in any of the biopsy caps disclosed herein. For example, FIG. 9 illustrates securing member 740, which may be similar to securing members 140/240 and/or other securing members disclosed herein. Securing member 740 may include a pair of locking tabs 750a/750b that may be fitted onto and secured to port 20. Tabs 750a/750b, which may be similar to tabs 150a/150b and/or 250a/250b, may be configured to snap onto port 20. In some embodiments, tabs 750a/750b may include a ridge 751. Ridge 751 may help to hold securing member 740 onto port 20 and/or mate with another ridge 751 or groove that may be formed on port 20.

Figure 10:
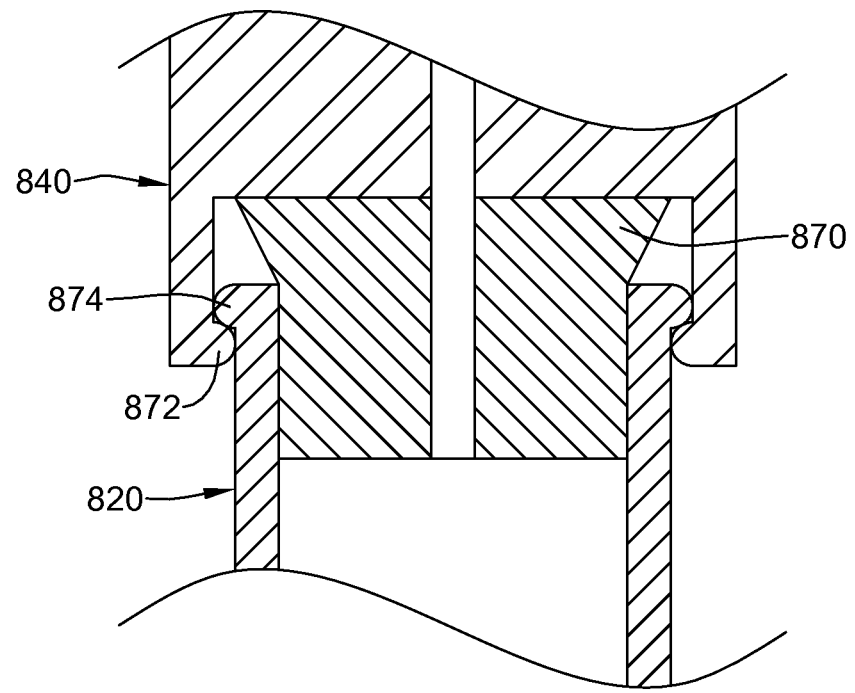
FIG. 10 is a perspective view of another example securing member.

FIG. 10 illustrates another example securing member 840, which may be utilized in conjunction with any of the caps disclosed herein. Securing member 840 may include a plug or stopper 870 that may be configured to fit within port 820 in a manner similar to a cork or elastomeric stopper. Indeed, plug 870 may be made from similar materials including, for example, silicone, cork, an elastomer, rubber, and the like or other suitable sealing materials. In addition, securing member 840 may also include a ridge 872 that helps to hold securing member 840 in place, for example, adjacent a ridge 874 formed on the end of port 820. Alternatively, port 820 may include a groove (not shown) that is configured to mate with ridge 872.

Figure 11:
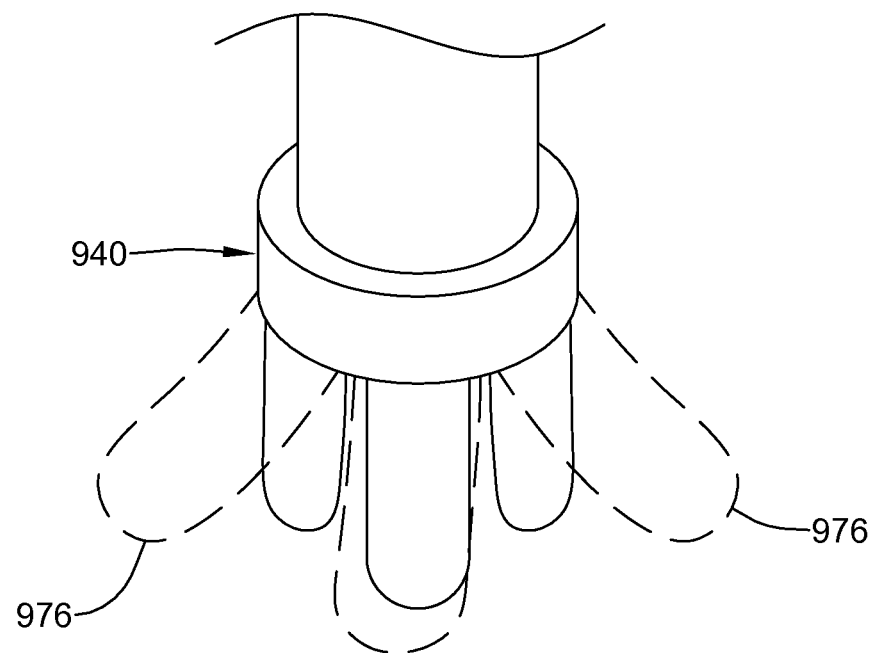
FIG. 11 is a perspective view of another example securing member.

FIG. 11 illustrates another example securing member 940. Securing member 940 may include a plurality of leaf-like fingers 976. Fingers 976 may be configured to shift between a first or "open" position (depicted in phantom) and a second or "closed" position, the later being used to hold securing member 940 onto an access port. In some embodiments, fingers 976 may grasp onto or hold onto a side portion of the access port and/or the endoscope. Alternatively, fingers 976 may wrap around (e.g., the back side of) the access port and/or endoscope.

In at least some embodiments, fingers 976 are made from a deformable material that allows them to shift between the first and second positions and hold the desired shape/position. Leaf-like fingers 976 may be utilized alone as a securing member 940, as shown, or as a secondary attachment means by combining them with other securing members 940.

Figure 12A:
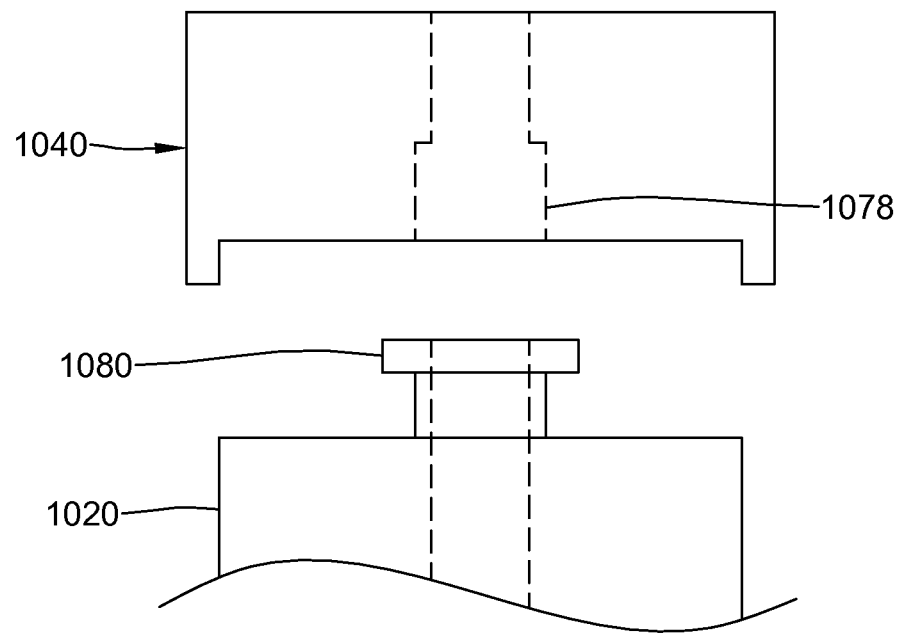
FIG. 12A is a perspective view of another example securing member in a first configuration.
Figure 12B:
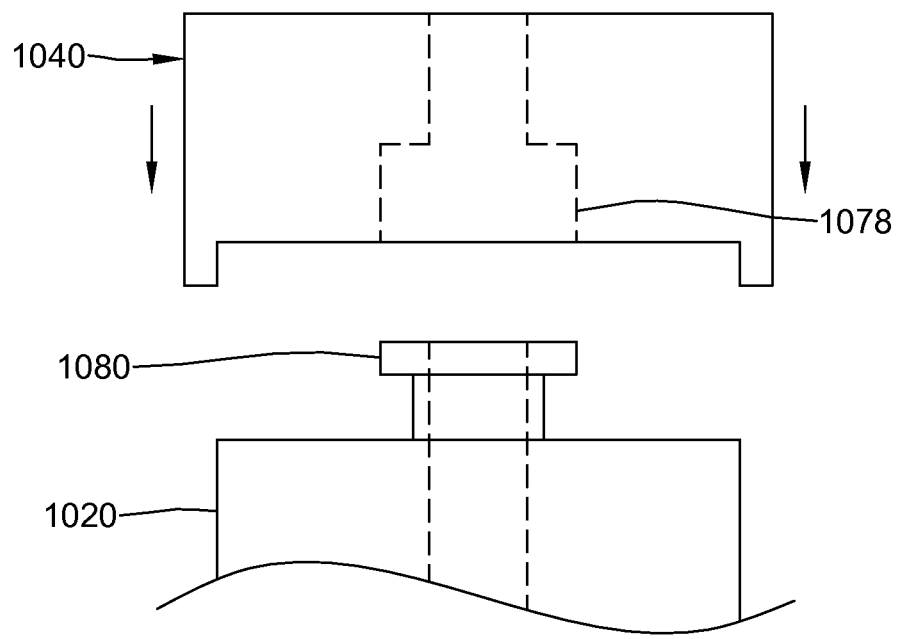
FIG. 12B is a perspective view of the example securing member illustrated in FIG. 12A in a second configuration.

FIGS. 12A and 12B illustrate another example securing member 1040. Securing member 1040 may include an end with a deformable or flexible opening 1078 that is configured to shift between a narrowed configuration (illustrated in FIG. 12A) and an expanded configuration (illustrated in FIG. 12B). When in the expanded configuration, opening 1078 may be fitted over a portion of port 1020, for example, such as a flange or ridge 1080 on port 1020. Shifting may be accomplished by the nature of the material in which opening 1078 is formed. For example, the end of securing member 1040 may include a flexible polymer, an elastomer, silicone, rubber, and the like, or any other suitable material that may be resilient enough to undergo the necessary shifts in size. Once seated, opening 1078 may shift or partially shift back to the narrowed configuration and seal about port 1020.

Figure 13:
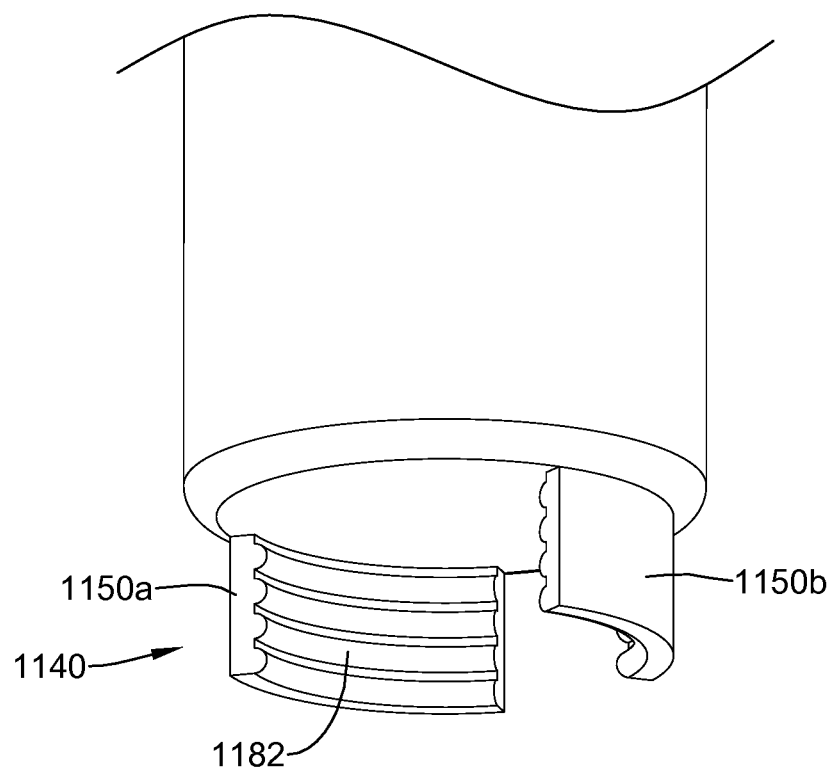
FIG. 13 is a perspective view of another example securing member.

FIG. 13 illustrates another example securing member 1140 that may be similar in form and function to other securing members disclosed herein. Securing member 1140 may include a plurality of tabs 1150a/1150b having threads 1182 formed thereon. Other than having threads 1182 formed thereon, tabs 1150a/1150b may be similar to tabs 150a/150b, tabs 250a/250b, and/or tabs 750a/750b. Securing member 1140 may be configured to attach to an access port by threading onto the port (e.g., port 20 or a version of port 20 with corresponding threads).

Figure 14:
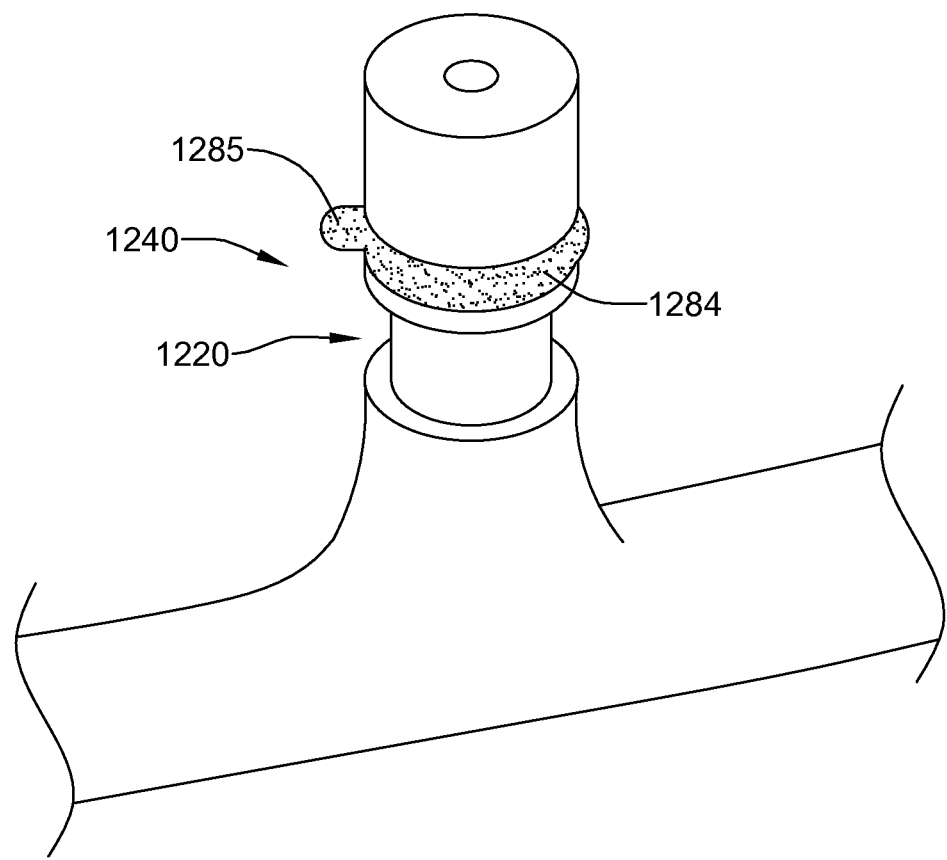
FIG. 14 is a perspective view of another example securing member.

FIG. 14 illustrates another example securing member 1240 that may be similar in form and function to other securing members disclosed herein. Securing member 1240 may include a "quick release" pull tab 1284. Tab 1284 may be disposed on the end of port 1220. In some embodiments, tab 1284 may include an adhesive that is configured to form a seal at port 1220 and thus hold the biopsy cap onto port 1220. In addition, the adhesive in tab 1284 may be disrupted or pulled thereon, for example at a pull point 1285, so that the cap can be quickly and easily removed from port 1220, as desired.

In addition to those securing members disclosed herein, any of the caps disclosed herein may alternatively include other suitable securing members without departing from the spirit of the invention. For example, other securing members may include, but are not intended to be limited to, lock and key designs, slidable or depressible button locks that may catch or otherwise secure onto the port, long sleeves that are disposed over the port, fasteners that includes adhesives including pressure-sensitive adhesives (e.g., that may be analogous to those used on canning lids), and the like. The same may also be true of the various locking members disclosed below.

FIGS. 15A-20 illustrate example locking members that may be utilized with any of the biopsy caps disclosed herein. These locking members may be attached to a biopsy cap at any suitable position thereon and they may be used to secure the position of a medical device (e.g., a guidewire, catheter, etc.) relative to the cap (and/or endoscope 10). Just like was the case for the securing members disclosed above, some of the additional cap structure is omitted from FIGS. 15A-20 for simplicity purposes. However, it can be appreciated that any of the locking members shown and contemplated may be attached to a biopsy cap using conventional methods to achieve the desired result.

Figure 15A:
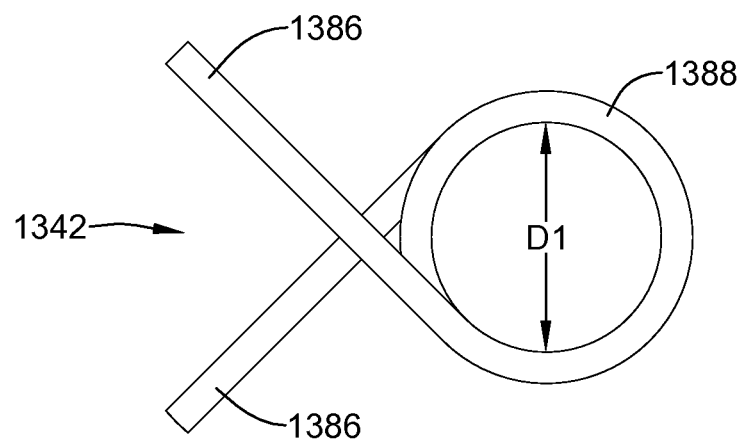
FIG. 15A is a perspective view of an example locking member in a first configuration.
Figure 15B:
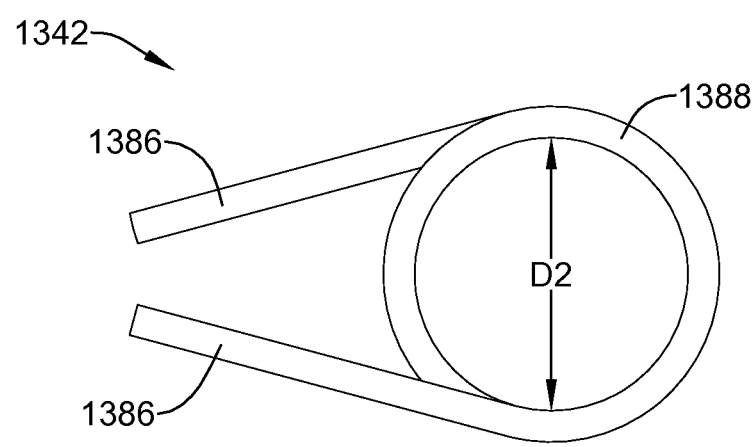
FIG. 15B is a perspective view of the example locking member illustrated in FIG. 15A in a second configuration.

FIGS. 15A and 15B illustrate locking member 1342, which may be configured to shift between a first configuration (as illustrated in FIG. 15A) and a second configuration (as illustrated in FIG. 15B). Locking member 1342 may include a pair of actuating arms 1386 that, when actuated, shift a locking ring 1388 from the first or smaller configuration that defines a smaller diameter D1 to the second or larger configuration that defines a larger diameter D2. Locking member 1342 may be described as being a spring clip or spring wing as locking ring 1388 may include a plurality of loops of material with a spring-like configuration. The extra portion or loops of the "spring" may be utilized to accommodate the expansion in size of ring 1388. In at least some embodiments, locking member 1342 may have a form similar to a clip that may be used to secure weights onto a barbell.

Although not shown, locking member 1342 may be attached to a biopsy cap at any suitable location using any suitable means. For example, a portion of arms 1386 and/or ring 1388 may be directly attached to a cap. Alternatively, an arm or member may extend from the cap that attaches to locking member 1342. In still other embodiments, locking member 1342 may include an additional structure such as a clip to removably secure locking member 1342 to a cap. These later embodiments of locking member 1342 and other locking members may be desirable because they may allow different types of locking members to be "mixed and matched" based on their particular applicability to a given intervention. It can be appreciated that a number of securing members are also contemplated that take a form similar to locking member 1342 and that are used to secure a cap to a port.

Figure 16:
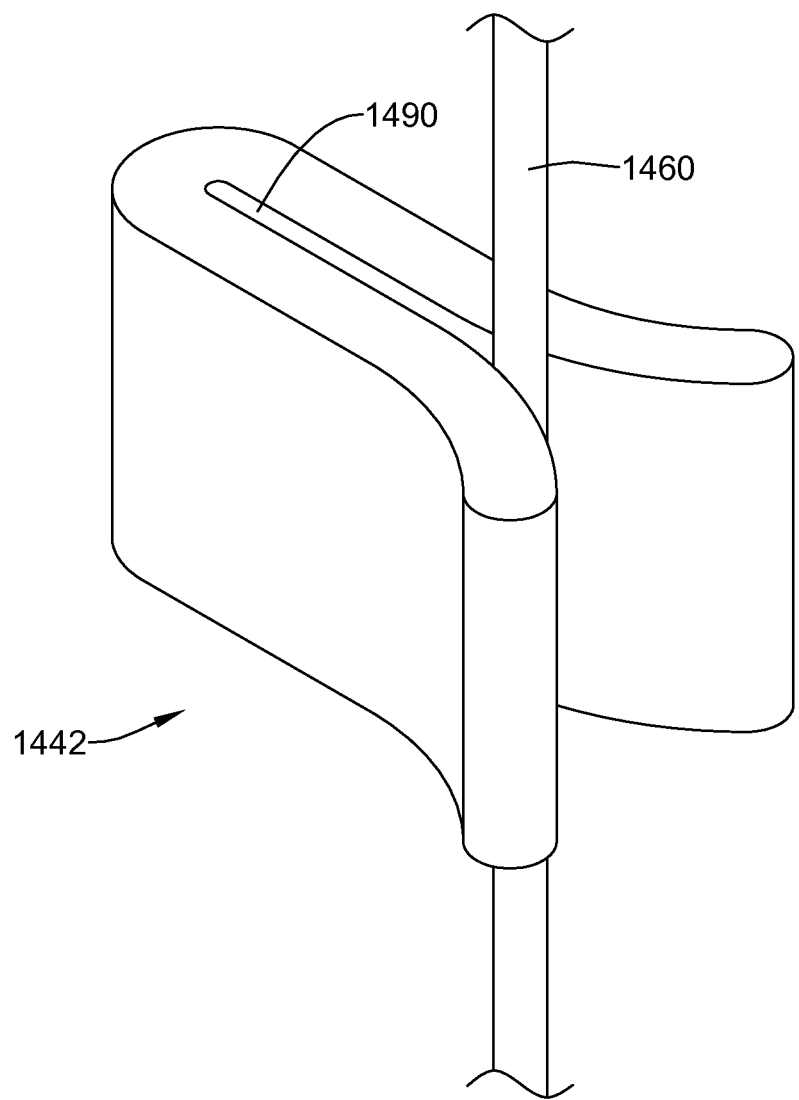
FIG. 16 is a perspective view of another example locking member.

FIG. 16 illustrates another example locking member 1442, which may be used with any of the biopsy caps disclosed herein. Locking member 1442 may have a wedge-like shape and may have a channel or groove 1490 formed therein where device 1460 (e.g., a guidewire, catheter, etc.) can be disposed therein and held by friction. Just like the other locking members disclosed herein, locking member 1442 may be attached to a biopsy cap at any suitable location using any suitable means.

Figure 17A:
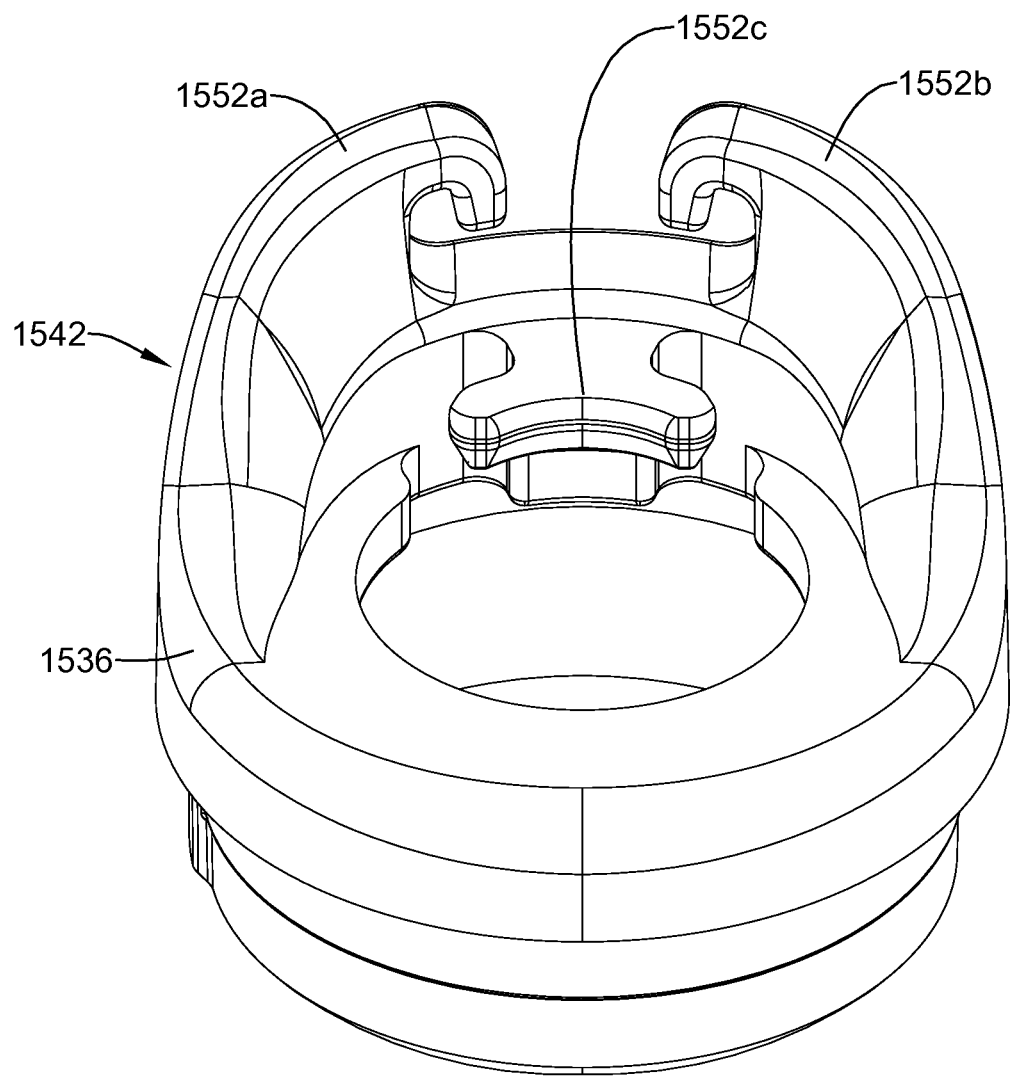
FIG. 17A is a perspective view of another example locking member.

FIG. 17A illustrates another example locking member or locking assembly 1542, which may be used with any of the biopsy caps disclosed herein. Locking member 1542 may include a plurality of locking features including, for example, a pair of arms 1552*a*/1552*b* that are coupled to or integrally formed on shell 1536. Arms 1552*a*/1552*b* may be shaped in a manner that may allow them to secure the position of a device (e.g., a guidewire, catheter, etc.). For example, arms 1552*a*/1552*b* may include one or more bends, hooks, grooves, and/or the like. Locking member 1542 may also include another locking structure or arm 1552*c* that may be disposed below arms 1552*a*/1552*b*. By virtue of having this position, arm 1552*c* may be used in conjunction with one or more of arms 1552*a*/1552*b* to allow the device to be wrapped around the desired combination of structures 1552*a*/1552*b*/1552*c*.

Figure 17B:
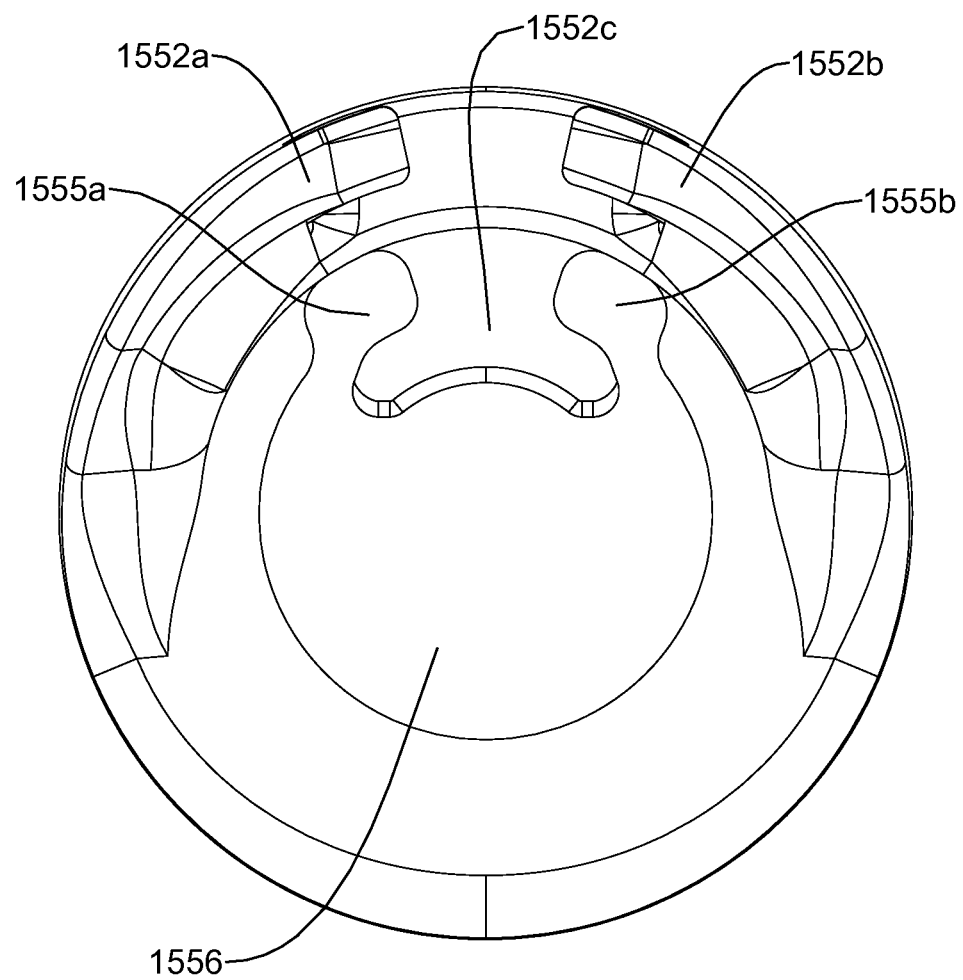
FIG. 17B is a perspective view of an alternative locking member to that depicted in FIG. 17A.

As illustrated in FIG. 17B, which is a rotated view of the locking member 1542 of FIG. 17A, the arm 1552*c* is shaped to create slotted openings 1555*a*/1555*b* in cooperation with the opening 1556 in the upper end of the shell. In some embodiments, the slotted opening is shaped with a narrowed opening which expands into a larger instrument holding area that has contoured surfaces for easy placement and removal of an instrument.

Figure 17C:
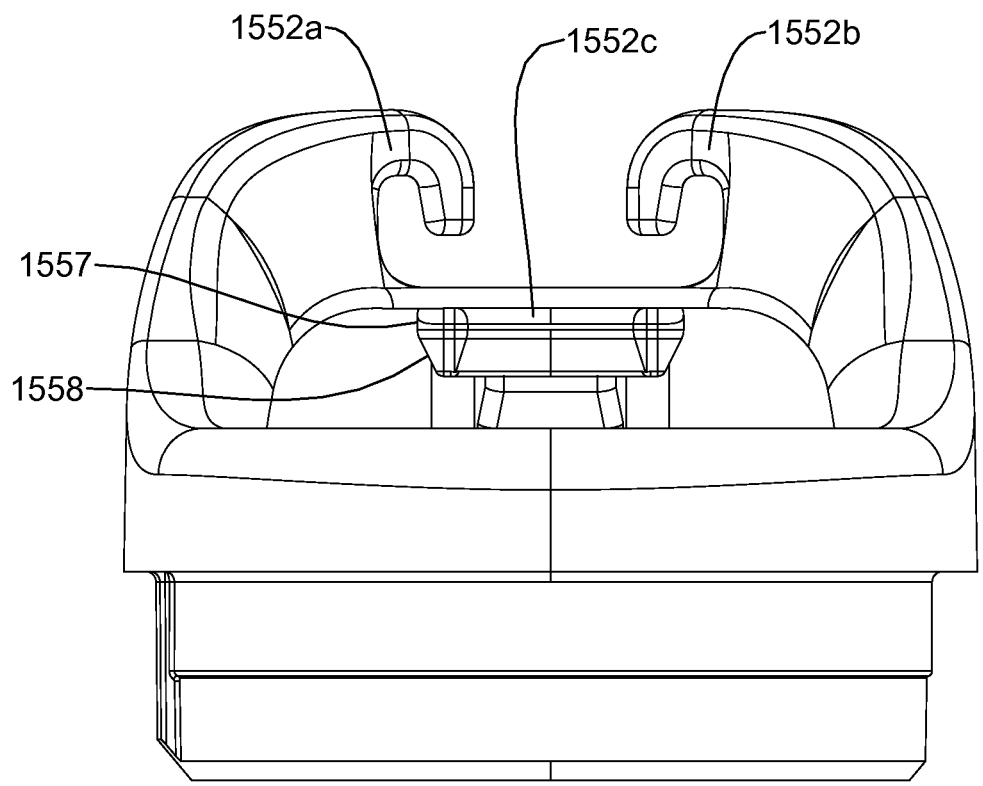
FIG. 17C is a perspective view of the alternative locking member of FIG. 17B showing further details.

FIG. 17C provides further detail of an exemplary design of arm 1552*c*. As indicated, the surface of arm 1552*c* is contoured to provide easy movement of a guidewire or instrument around its surface. Further, the edge 1557 includes an open shoulder 1558 along the lower portion of the lateral surface of arm 1552*c*. This surface helps prevent instruments from catching on arm 1552*c*.

Figure 18:
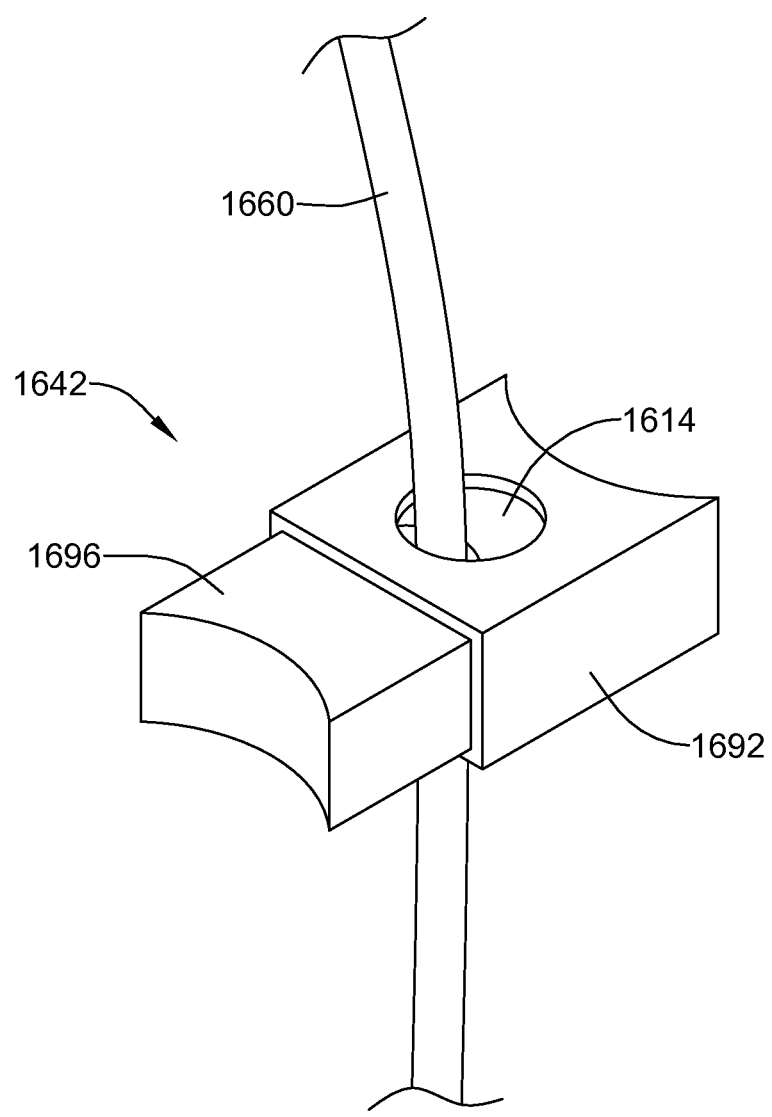
FIG. 18 is a perspective view of another example locking member.

FIG. 18 illustrates another example locking member 1642, which may be used with any of the biopsy caps disclosed herein. Locking member 1642 may include a base 1692 having an opening 1614 formed therein. Device 1660 may extend through opening 1614. A spring button 1696 may be attached to base 1692. Spring button 1696 may be coupled to a spring (not shown) that biases a portion of button 1696 (e.g., a rear portion of button 1696 that may be disposed within base 1692 on the opposite side of opening 1614) into opening 1614, thereby "closing" or "locking" opening 1614. Depressing button 1696 may overcome the bias and open opening 1614 so that device 1660 can be extended therethrough. Releasing button 1696 allows the spring to press button 1696 back into the biased position and lock the position of device 1660.

A number of different configurations are contemplated for locking member 1642. For example, locking member 1642 may have a barrel-like or cylindrical shape rather than the more squared or rectangular shape as shown. In addition, locking member 1642 may include a lock that can reversibly hold button 1696 in the desired position such as, for example, the locked position.

Figure 19:
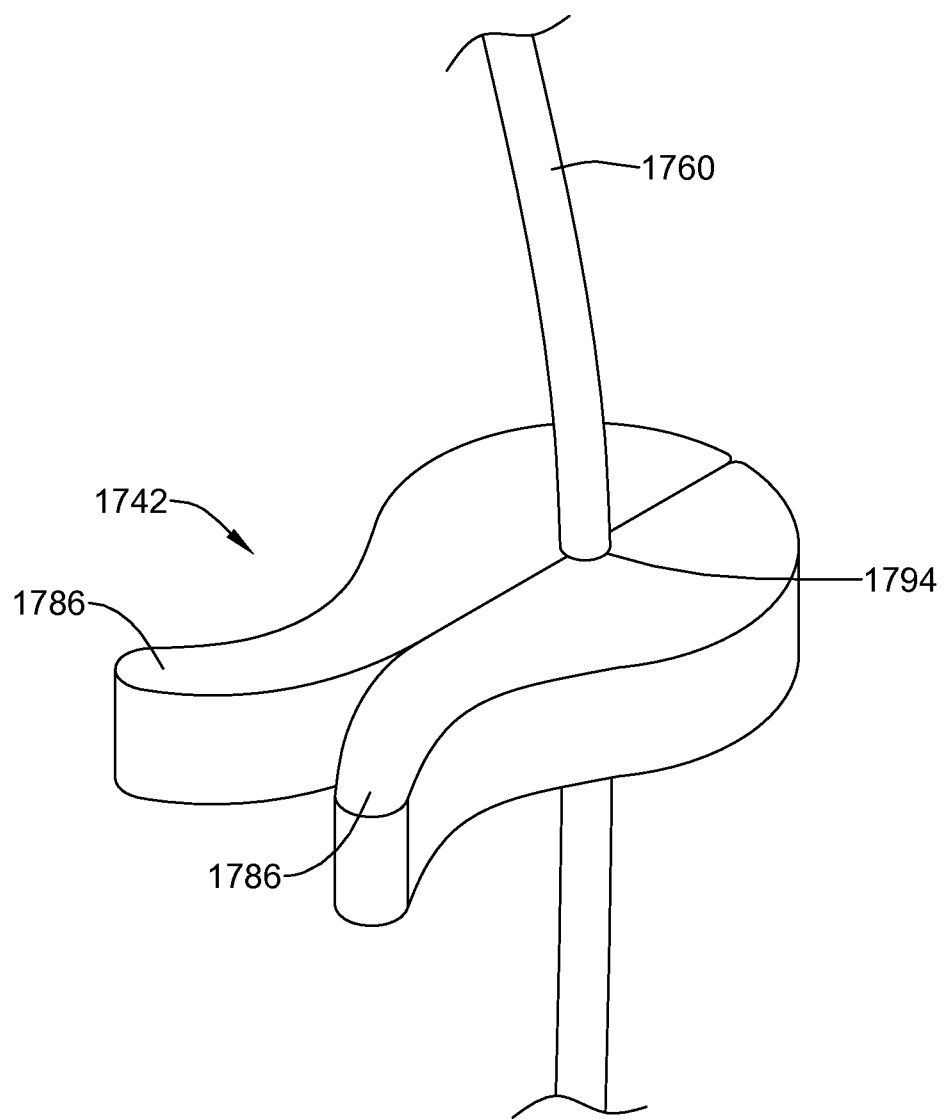
FIG. 19 is a perspective view of another example locking member.

FIG. 19 illustrates another example locking member 1742, which may be used with any of the biopsy caps disclosed herein. Locking member 1742 may include a pair of arms 1786 that can be actuated to open/close opening 1794 to secure device 1760. Locking member 1742 may function in a manner similar to a clothespin. As such, locking member 1742 may include a spring or other biasing member (not shown) that holds it in either the open (e.g., "unlocked") or closed (e.g., "locked") positions.

Figure 20:
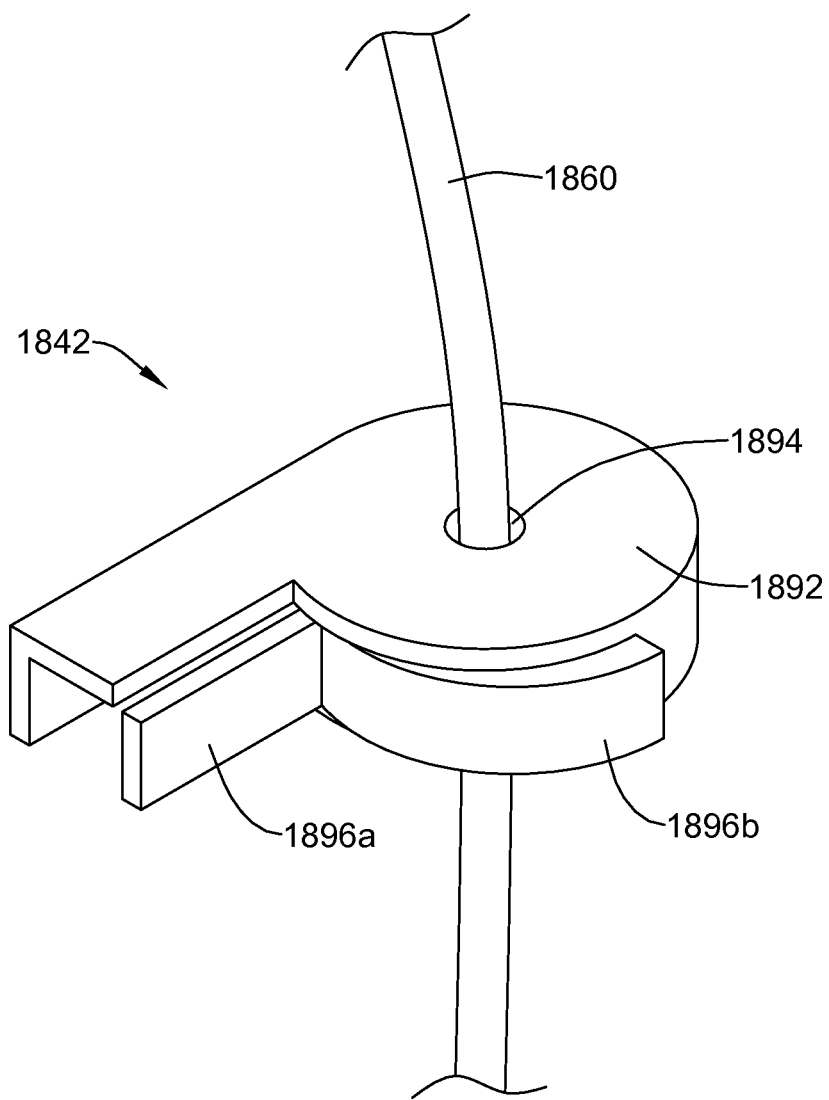
FIG. 20 is a perspective view of another example locking member.

FIG. 20 illustrates another example locking member 1842, which may be used with any of the biopsy caps disclosed herein. Locking member 1842 may include a base 1892 having opening 1894 formed therein. Device 1860 may extend therethrough. A pair of buttons 1896*a*/1896*b* may be attached to base 1892 for opening/closing opening 1894. For example, one of the buttons (e.g., button 1896*b*) may be depressed to "lock" device 1860 while the other button (e.g., button 1896*a*) may be depressed to open or "unlock" device 1860.

Figure 21A:
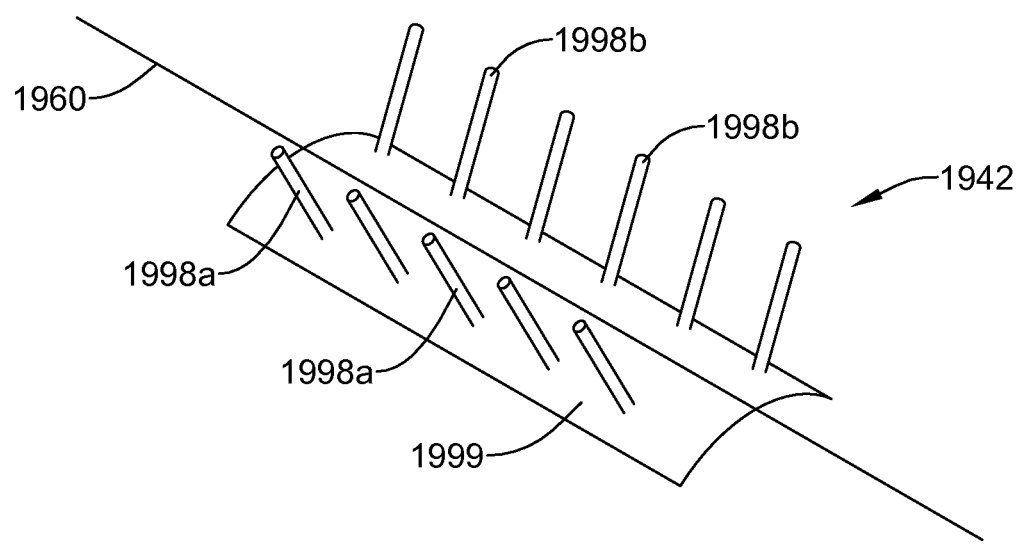
FIG. 21A is a perspective view of another example locking member in a first configuration.
Figure 21B:
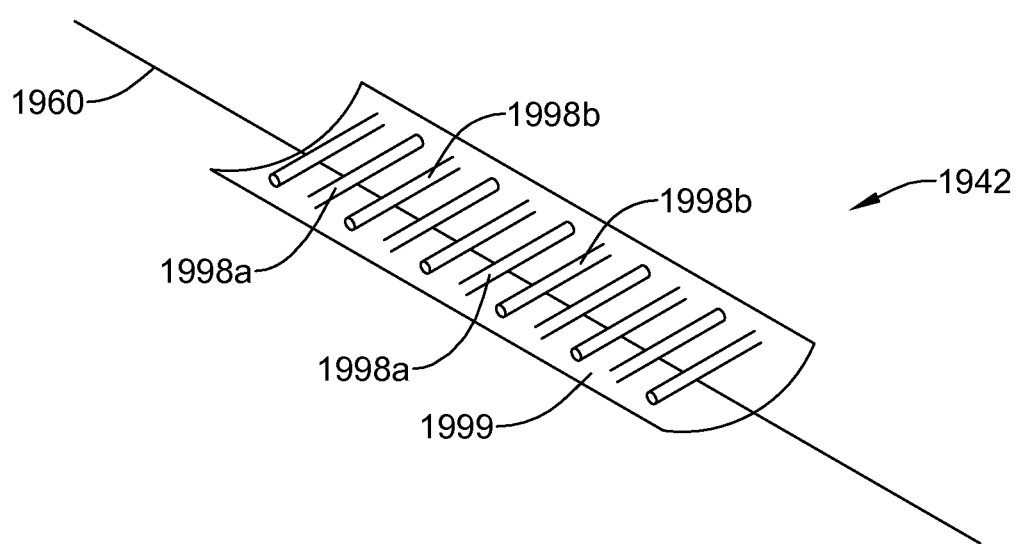
FIG. 21B is a perspective view of the example locking member illustrated in FIG. 21A in a second configuration.
Figure 22A:
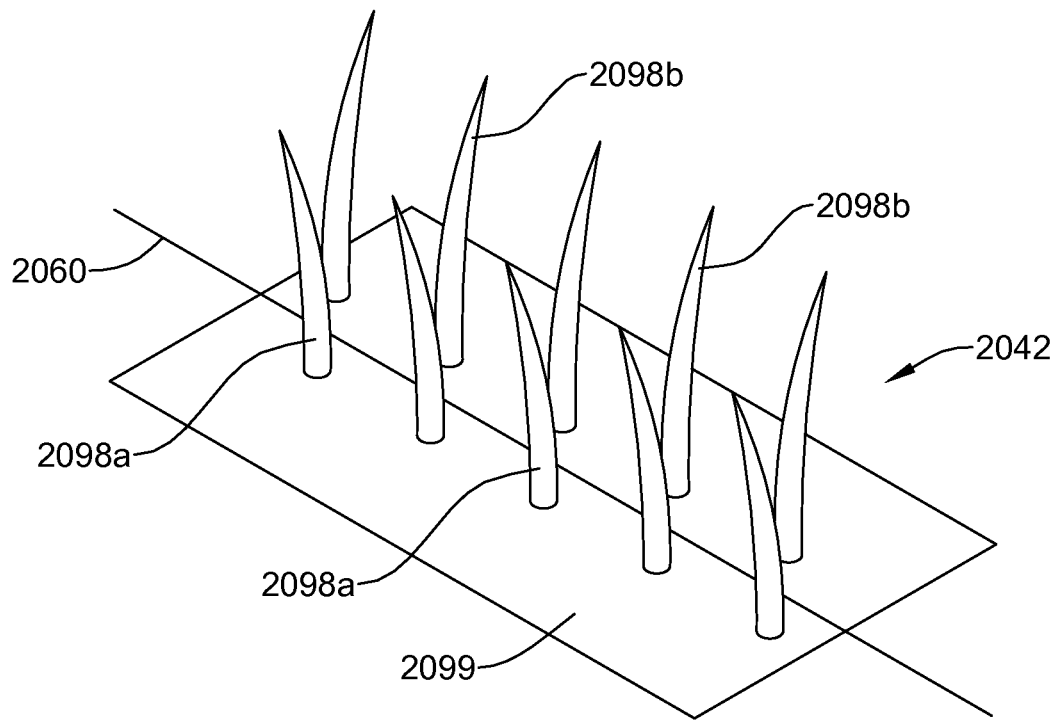
FIG. 22A is a perspective view of another example locking member in a first configuration.
Figure 22B:
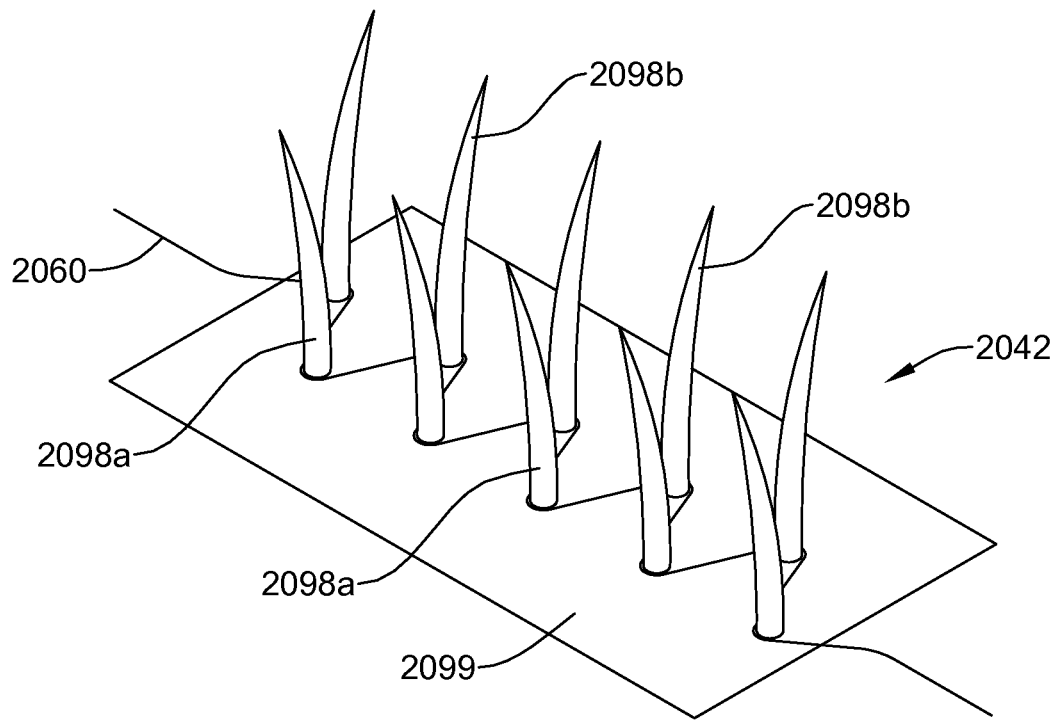
FIG. 22B is a perspective view of the example locking member illustrated in FIG. 22A in a second configuration.

FIGS. 21A and 21B illustrate locking member 1942, which may be configured to shift between a first or open configuration (as illustrated in FIG. 21A) and a second or closed configuration (as illustrated in FIG. 21B). Locking member 1942 may include a pair of opposing sets of fingers 1998*a*/1998*b* coupled to a base 1999 that are configured to shift from the upright or open first position to the horizontal or flat second configuration, the later being configured to secure the position of device 1960. FIGS. 22A and 22B illustrate locking member 2042, which may be similar in form and function to locking member 1942. Locking member 2042 may include a pair of opposing sets of fingers 2098*a*/2098*b* coupled to a base 2099. Device 2060 may extend through fingers 2098*a*/2098*b* as shown in FIG. 22A, which may hold device 2060 in place, for example, by friction. Alternatively, device 2060 may be wrapped around fingers 2098*a*/2098*b*, as shown in FIG. 22B.

In some embodiments, bases 1999 and/or 2099 may be generally planar. In other embodiments, bases 1999 and/or 2099 may be curved so as to be convex, concave, or have another shape. Moreover, bases 1999 and/or 2099 may change from one shape to another upon actuation of fingers 1998*a*/1999*b* and/or 2098*a*/2098*b*. For example, bases 1999 and/or 2099 may be generally planar when fingers 1998*a*/1999*b* and/or 2098*a*/2098*b* are in the open position and bases 1999 and/or 2099 may shift to a concave shape when fingers 1998*a*/1999*b* and/or 2098*a*/2098*b* shift to the flat configuration. Alternatively, bases 1999 and/or 2099 may shift from concave to planar, convex to planar, planar to convex, etc.

A number of alternatives are also contemplated for fingers 1998*a*/1999*b* and/or 2098*a*/2098*b*. For example, fingers 1998*a*/1999*b* and/or 2098*a*/2098*b* may be interconnected so that the shifting of one finger results in the shifting of all the fingers. Alternatively, flaps may be used instead of or in addition to fingers 1998*a*/1999*b* and/or 2098*a*/2098*b* that extend down at least a portion of the length of bases 1999 and/or 2099 and that are configured to shift between an open and a closed configuration.

Base 1999/2099 of locking members 1942/2042 may desirably add a surface substrate that may allow these devices to be attached to a biopsy cap. In some embodiments, base 1999/2099 may include a strip of polymer or plastic that can be bonded to a biopsy cap with a permanent adhesive. In other embodiments, base 1999/2099 may be configured to be removably attached to the biopsy cap. For example, a removable or temporary adhesive may be used, base 1999/2099 may be "velcroed" onto the cap, etc.

Figure 23A:
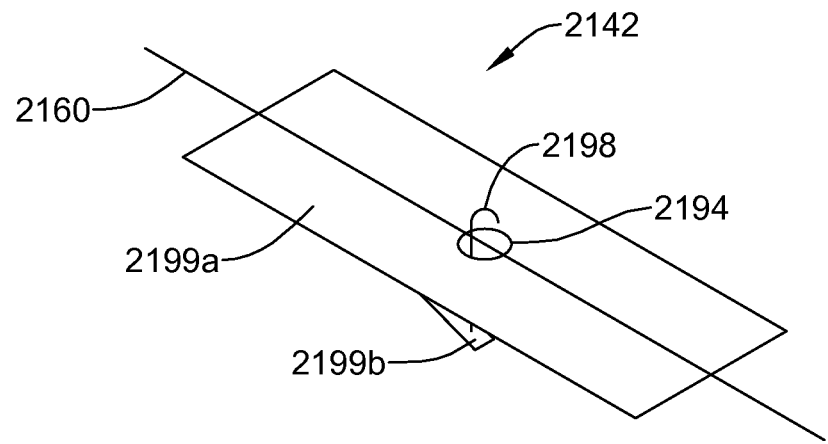
FIG. 23A is a perspective view of another example locking member in a first configuration.
Figure 23B:
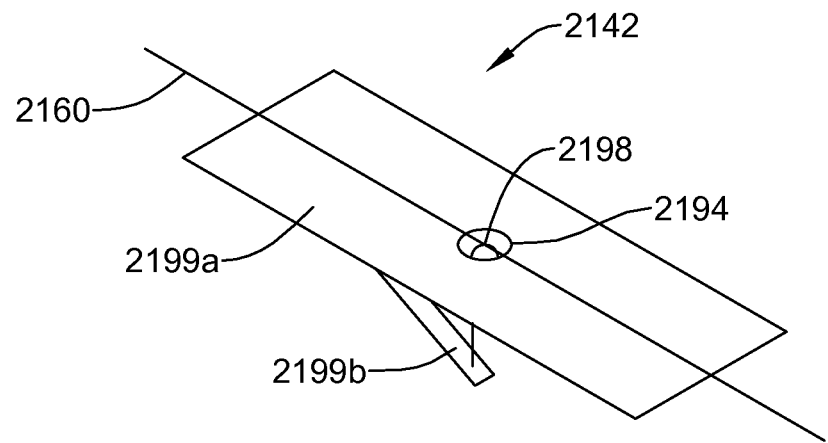
FIG. 23B is a perspective view of the example locking member illustrated in FIG. 23A in a second configuration.

FIGS. 23A and 23B illustrate locking member 2142, which may be configured to shift between a first configuration (as illustrated in FIG. 23A) and a second configuration (as illustrated in FIG. 23B). Locking member 2142 may include a base 2199a including a platform region 2199b. Region 2199b may include a hook-like extension 2198 that extends through an opening 2194 in base 2199a and that can grasp device 2160 when actuated (as illustrated in FIG. 23A). Region 2199b may be hingedly connected to base 2199a so that region 2199b can be moved up or down, as desired, to engage device 2160. In alternative embodiments, multiple hook-like extensions 2198 may be utilized. Furthermore, hook-like extensions 2198 having different shapes may also be utilized such as longer hooks, wider hooks, two or more opposing hooks, eyelets, etc.

Figure 24:
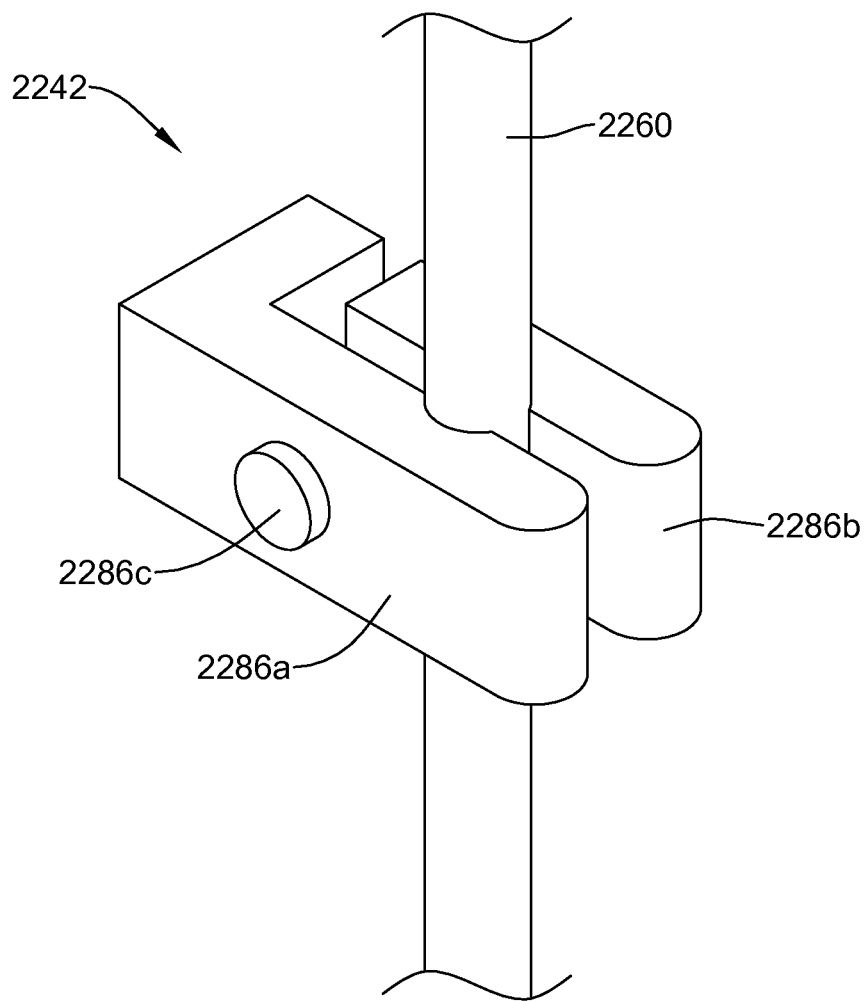
FIG. 24 is a perspective view of another example locking member.

FIG. 24 illustrates another example locking device 2260, which may be used with any of the biopsy caps disclosed herein. Device 2260 may include a pair of arm segments 2286a/2286b coupled together by a linkage 2286c. Linkage 2286c may be slidable within one of the arm segments 2286a/2286b so that arms 2286a/2286b can be brought into closer contact with one another by pinching together arms 2286a/2286b and locking the position of device 2260. Manually moving arms 2286a/2286b further apart may release device 2260.

In some embodiments, one or more additional locking members may be added to a cap. The additional locking member may take any suitable form including any of those disclosed herein. Adding the locking members may include fastening, snapping on, or hingedly connecting an external locking member assembly onto the cap. Some additional discussion of wire or other locking devices which may be suitable for use with a biopsy cap may include U.S. Patent Application Pub Nos. US20060229496A1, US20050148820A1, and US20040106852A1 as well as U.S. Pat. Nos. 7,060,052, 7,037,293, 6,893,393, 6,663,597, and 6,096,009, the entire disclosures of which are herein incorporated by reference.

The various caps as well as the various components thereof may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In at least some embodiments, portions or all of the structures disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of endoscope 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of endoscope 10 or the various components thereof to achieve the same result.

In some embodiments, a degree of MRI compatibility may be imparted into the structures disclosed herein. For example, to enhance compatibility with Magnetic Resonance Imaging (MRI) machines, it may be desirable to make a portion of endoscope 10 in a manner that would impart a degree of MRI compatibility. For example, a portion of endoscope 10 may be made of a material that does not substantially distort the image and create substantial artifacts (artifacts are gaps in the image). Certain ferromagnetic materials, for example, may not be suitable because they may create artifacts in an MRI image. A portion of endoscope 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In addition, portions or components of the structures (including the various securing members, locking members, etc.) disclosed herein may be coated with a relatively soft material that may improve grip such as a thermoplastic elastomer. The coating may or may not include additional features that may improve grip such as ridges, surface textures, bumps, grooves, projections, etc.

Furthermore, the various structures disclosed herein may be designed for single use or may be designed for repeated uses. Thus, the structures disclosed herein may be manufactured from materials that can withstand multiple sterilizations and/or cleanings This may be true of entire caps, as disclosed herein, or any of the various features of any of the caps.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A biopsy cap for use in an endoscopic instrument, the cap comprising:
    a base having a securing member for securing the cap to a port on the endoscopic instrument;
    an outer shell having one or more apertures and a locking member coupled to the outer shell;
    a passive seal member disposed within the outer shell, wherein the passive seal member includes a plurality of fingers extending radially inward in a distal direction from the outer shell;
    wherein each of the plurality of fingers includes a pad attached thereto, the plurality of fingers arranged in opposing fashion such that opposing fingers urge the pads against each other when a medical device is absent from the passive seal member and urge the pads against the medical device when the medical device extends through the passive seal member.

2. The assembly of claim 1, wherein at least some of the plurality of fingers include a sealing material attached thereto.

3. The assembly of claim 1, wherein the cap may include a sealing substance disposed adjacent the plurality of fingers.

4. The assembly of claim 3, wherein the sealing substance includes a fluid or gel.

5. The assembly of claim 1, wherein at least some of the plurality of fingers include an end surface with a tether attached thereto.

6. The assembly of claim 1, wherein the one or more apertures include an entrance aperture and exit aperture, and wherein a channel extends between the entrance aperture and the exit aperture, and wherein at least some of the fingers extend into the channel.

7. The assembly of claim 6, wherein the channel is configured to provide access to a working channel of an endoscope.

8. The assembly of claim 7, wherein the plurality of fingers are configured to seal against a medical instrument extending through the channel.

* * * * *